(12) United States Patent
Visuri et al.

(10) Patent No.: US 7,087,719 B2
(45) Date of Patent: Aug. 8, 2006

(54) METHOD FOR THE CRYSTALLIZATION OF HUMAN SERUM ALBUMIN

(75) Inventors: Kalevi Visuri, Kirkkonummi (FI); Sinikka Uotila, Espoo (FI); Scott P. Fulton, Middleton, WI (US); Daniel E. Couto, Chelsea, MA (US)

(73) Assignee: GTC Biotherapeutics, Inc., Framingham, MA (US)

( * ) Notice: Subject to any disclaimer, the term of this patent is extended or adjusted under 35 U.S.C. 154(b) by 166 days.

(21) Appl. No.: 10/300,233

(22) Filed: Nov. 19, 2002

(65) Prior Publication Data

US 2004/0097710 A1 May 20, 2004

(51) Int. Cl.
*C07K 17/00* (2006.01)
*A23J 1/00* (2006.01)
*A61K 38/00* (2006.01)

(52) U.S. Cl. ............... 530/363; 530/362; 530/364; 530/402; 530/412; 530/417; 530/418; 530/419; 530/421; 530/829; 530/830; 514/2

(58) Field of Classification Search ............ 530/362, 530/364, 402, 412, 417, 418, 419, 421, 829, 530/830; 514/2
See application file for complete search history.

(56) References Cited

U.S. PATENT DOCUMENTS

| 4,683,195 A | 7/1987 | Mullis et al. |
| 5,585,466 A | 12/1996 | Carter |
| 2003/0036637 A1 | 2/2003 | Fulton |

FOREIGN PATENT DOCUMENTS

| EP | 0 357 857 A1 | 3/1990 |
| WO | WO 02101021 A1 | 12/2002 |

OTHER PUBLICATIONS

Remington's Pharmaceutical Sciences, 16th ed., Osol, A., editor; Mack, Easton Press., Chapter 89, 95-100, 1035-1038, 1411,-1712, 1980.
Culture Of Animal Cells (R. I. Freshney, Alan R. Liss, Inc., 1987).
DNA Cloning, vols. I and II (D. N. Glover ed., 1985).
Gene Transfer Vectors For Mammalian Cells (Cold Spring Harbor Laboratory, J. H. Miller and M. P. Calos eds., 1987).
Handbook Of Experimental Immunology, vols. I-IV (D. M. Weir and C. C. Blackwell, eds., 1986).
Immobilized Cells And Enzymes (IRL Press, 1986).
Immunochemical Methods In Cell And Molecular Biology (Mayer and Walker, eds., Academic Press, London, 1987).
Introduction to Pharmaceutical Dosage Forms, 4th Edition, Lea & Febiger, Philadelphia (1985).
Manipulating the Mouse Embryo, (Cold Spring Harbor Laboratory Press, Cold Spring Harbor, N.Y., 1986).
Methods In Enzymology, vols. 154 and 155 (Wu et al. eds.).
Molecular Cloning. A Laboratory Manual, 2nd Ed., Sambrook, Fritsch and Maniatis (Cold Spring Harbor Laboratory Press: 1989).
Nucleic Acid Hybridization (B. D. Hames & S. J. Higgins eds. 1984).
Oligonucleotide Synthesis (M. J. Gait ed., 1984).
Transcription And Translation, (B. D. Hames & S. J. Higgins eds. 1984).
Adair et al., Biochem. J., 24, pp. 993-1011 (1930).
Adair et al., Crystallization of human serum albumin, Nature, 23, p. 307 (1935).
Alexander et al., Eur. J. Biochem., 178, pp. 395-401 (1988).
Alexander et al., Nucleic Acids Res., 17, p. 6739 (1989).
Anderegg et al., J. Am. Chem. Soc. 77, p. 2927 (1955).
Andersson, "The Heterogeneity Of Bovine Serum Albumin," Biochim. Biophys. Acta., 117:pp. 115-133 (1966).
Bhattacharya et al., J. Biol. Chem., 275(49), p. 38731 (2000).
Bhattacharya et al., J. Mol. Biol. 303, p. 721 (2000).
Brignon et al., FEBS Lett., 188, pp. 48-55 (1977).
Brodersen et al., Scandinavian journal of clinical and laboratory investigation, 29(4), p. 433 (1972).
Campbell et al., Nucleic Acids Res., 12, pp. 8685-8697 (1984).
Carter DC, et al., *Preliminary Crystallographic Studies of Four Crystals Forms of Serum Albumin*, Eur. J. Biochem., 226: pp. 1049-1052 (1994).
Carter DC, et al., *Three-Dimensional Structure of Human Serum Albumin*, Science, 244: pp. 1195-1198 (1989).
Carter et al., *Structure of human serum albumin*, Science, 249, p. 302 (1990).
Cochrane et al., *Human Albumin Administration In Critically III Patients: Systematic Review Of Randomized Controlled Trials*, Br. Med. J., 317: pp. 235-240 (1998).
Cohn EJ, et al., *Preparation and Properties of Serum and Plasma Proteins. XIII. Crystallization of Serum Albumins from Ethanol-Water Mixtures*, J. Am. Chem. Soc., 69: pp. 1753-1761 (1947).

(Continued)

Primary Examiner—Jon Weber
Assistant Examiner—Abdel A. Mohamed
(74) Attorney, Agent, or Firm—Byron V. Olsen

(57) ABSTRACT

The present invention relates to the purification and production of human albumin from various sources through crystallization and repeated crystallization. Basic features of the invented process include providing specific reaction conditions and precipitating reagents to maximize albumin crystallization. Solubility diagrams are utilized as the basis for process control of the invented method. The current invention specifically controls phosphate concentration, pH and temperature to precisely guide crystallization kinetics and crystal yield.

51 Claims, 14 Drawing Sheets

OTHER PUBLICATIONS

Cohn EJ, et al., "*Preparation And Properties Of Serum And Plasma Proteins. IV. A System For The Separation Into Fractions Of The Protein And Lipoprotein Components Of Biological Tissues And Fluids*," J. Am. Chem. Soc., 68: pp. 459-475 (1946).

Cohn et al., A system for the separation of the components of human blood: quantitative procedures for the separation of the protein components of human plasma, J. Am. Chem. Soc., 72, p. 465 (1950).

Copelin C. et al., Practical Points In The Use Of Albumin For Hypovolemia, J Peranesth Nurs., 13: pp. 118-120 (1998).

Curry et al., Nat. Struct. Biol. 5(9), pp. 827-835 (1998).

Curry et al., Biochim Biophys Acta 1441, pp. 131-140 (1999).

Dale et al., *G Protein-Coupled Receptor Kinase-Mediated Desensitization of Metabotropic Glutamate Receptor 1A Protects Against Cell Death*, J. Biol Chem; 275: pp. 38213-38220 (2000).

Emerson, TE, *Unique Features of Albumin: A Brief Review*, Crit. Care Med., 17: pp. 690-693 (1989).

Goldwaser et al., *Association of Serum Albumin And Mortality Risk*, J. Clin. Epidemiol., 50: pp. 693-703 (1997).

Gore et al., *Colloid Infusions Reduce Glomerular Being filtered In Resuscitated Burn Patients*. J. Trauma., 3: pp. 356-360 (1996).

Gorodetsky et al., Gene, 66, pp. 87-96 (1988).

Hall, Biochem. J., 242, pp. 735-742 (1987).

Haupt et al., *Crystallization of Human Albumin Using Mineral Salts*, Klin Wochenschr, 45: pp. 726-729 (1967).

He et al., *Atomic structure and chemistry of human serum albumin*, Nature, 358, p. 209 (1992).

Hughes W L, *An Albumin Fraction Isolated From Human Plasma as a Crystalline Mercuric Salt*, J. Am. Chem. Soc., 69: pp. 1836-1837 (1947).

Hughes et al., *Crystallization of the mercury dimers of human and bovine mercaptalbumin*, J. Biol. Chem., 239: pp. 845-849 (1964).

Hughes et al., J. Am. Chem. Soc. 71, pp. 2476-2480 (1949).

Ivanov et al., Biol. Chem., Hoppe-Seyler 369, pp. 425-429 (1988).

Jamieson et al., Gene 61, pp. 85-90 (1987).

Jones et al., J. Biol. Chem., 260, pp. 7042-7050 (1985).

Kendall, Studies of human serum proteins II, Crystallization of human serum albumin, J. Biol. Chem., 138, pp. 97-109 (1941).

Klein GL, et al., *The Aluminum Content of Parenteral Solutions: Current Status*. Nutr. Rev., 49: pp. 74-79 (1991).

Kovalik SG, et al., *The Cardiac Effect of Altered Calcium Hemostasis After Albumin Resuscitation*, J. Trauma., 21: pp. 275-279 (1981).

Ledgerwood AM, et al., *Post-Resuscitation Hypertension, Etiology, Morbidity, And Treatment*. Arch. Surg., 108: pp. 531-538 (1974).

Lewin J, *Preparation and Properties of Serum and Plasma Proteins. XXX. Crystalline Derivatives of Human Serum Albumin and Certain Other Proteins*, J. Am. Chem. Soc., 73: pp. 3906-3911 (1951).

Low BW, *Preparation and Properties of Serum and Plasma Proteins. XXXIV. An X-Ray Study of Crystalline Human Serum Albumin Preparations*, J. Am. Chem. Soc., 74: pp. 4830-4834 (1952).

Low et., *Preparation and Properties of Serum and Plasma Proteins. XXXI. An Optical and Morphological Study of Some Crystalline Human Serum Albumin Preparations and of Their Derivatives*, J. Am. Chem. Soc., 73: pp. 3911-3916 (1951).

McClure et al., J. Mol. Biol., 83(4), pp. 551-555 (1974).

Mercier et al., J. Dairy Sci., 76, pp. 3079-3098 (1993).

Perbal, B., *A Practical Guide To Molecular Cloning* (1984).

Peters, T., *Serum Albumin*, Adv. Protein Chem., 37: pp. 161-245 (1985).

Petitpas et al., J. Biol. Chem., 276 (25), pp. 22804-22809 (2001).

Petitpas et al., J. Mol. Biol., 314, pp. 955-960 (2001).

Rainey et al., Pharmacology Of Colloids And Crystalloids, In: *The Pharmacologic Approach to the Critically Ill Patient*, (Chernow B. ed., Williams and Wilkins, Baltimore MD. Publ.), pp. 272-290 (1994).

Rao et al., *Preliminary X-Ray Investigation of an Orthorhombic Crystal Form of Human Plasma Albumin*, J. Biol. Chem., 251: pp. 3191-3193 (1976).

Richards et al., J. Biol. Chem., 256, pp. 526-532 (1981).

Roberts et al., Colloid Volume Expanders: Problems, Pitfalls, and Possibilities, Drugs, 55: pp. 621-630 (1998).

Sollenne et al., *Disruption Of The Tryptophan Binding Site In The Human Serum Albumin Dimer*, Arch. Biochem. Biophys., 207: pp. 264-269 (1981).

Stewart, Nucleic Acids Res., 12, pp. 389 (1984).

Sugio S, et al., *Crystal Structure of Human Serum Albumin At 2.5 A Resolution*, Protein Eng., 12: pp. 439-446 (1999).

Tullis JL, et al., *Albumin: Background and Use*. JAMA, 237: pp. 355-360 (1977).

Vermeulen LC et al., *Guidelines for the Use of Albumin, Nonprotein Colloids and Crystalloid Solutions*, Arch Intern Med., 155: pp. 373-379 (1995).

Vilotte et al., Biochimie, 69, pp. 609-620 (1987).

Yu-Lee & Rosen, J. Biol. Chem., 258, pp. 10794-10804 (1983).

Zunszain et al., Crystal structured analysis of human serum albumin complexed with hemin and fatty acid, BMC Struct. Biol.; 3 (2003).

METHOD FOR THE CRYSTALLIZATION OF HUMAN SERUM ALBUMIN

FIELD OF THE INVENTION

The present invention relates to methods for provide a highly reliable method and commercially viable method of crystallizing human albumin. More specifically, the current invention provides a method to produce crystalline human albumin purified from various albumin sources, specifically including from transgenic animals or other recombinant sources.

BACKGROUND OF THE INVENTION

The present invention is directed to an improved method of crystallizing human serum albumin ("hSA")(herein, hSA will be used interchangeably with the term human serum albumin). This process is preferably done to enhance purification procedures for recombinant hSA that can then be utilized in therapeutic applications or as an excipient in pharmaceutical preparations. With regard to pharmaceutical preparations human albumin as purified herein can be used as a therapeutic agent or as an excipient. In either case suitable formulations can be found in REMINGTON'S PHARMACEUTICAL SCIENCES (16th and 18th Eds., Mack Publishing, Easton, Pa. (1980 and 1990)), and in INTRODUCTION TO PHARMACEUTICAL DOSAGE FORMS (4th Edition, Lea & Febiger, Philadelphia (1985)), each of which is incorporated herein by reference.

For therapeutic applications of hSA the objective of albumin administration is primarily to maintain circulating plasma volume by maintaining the plasma colloid oncotic pressure, and to treat otherwise resistant severe edema by making intracavital and interstitial fluids move into the blood vessels.

Albumin products are used to achieve transient improvement of the condition by replenishing albumin in pathological conditions attributable to acute hypoproteinemia, and pathological conditions resulting from chronic hypoproteinemia which is resistant to other methods of treatment.

Albumin was the first natural colloid composition for clinical use as a blood volume expander, and it is the standard colloidal agent for comparison with other colloid products. Some of the specific medical indications in which albumin may be used to increase intravascular oncotic pressure and thereby expand intravascular volume in patients include: hypovolemic shock; severe burn injury; adult respiratory distress syndrome (ARDS); ascites; liver failure; pancreatitis and in patients undergoing cardiopulmonary bypass. (Cochrane et al., 1998). Albumin may also be used to treat neonatal hyperbilirubinemia, hypoproteinemia, and nephrotic syndrome. (Vermeulen et al., 1995).

The albumin portion of human blood serves three primary physiologic roles: (1) maintenance of plasma colloid osmotic pressure, (2) transport and sequestration of bilirubin, and (3) transport of fatty acids and other intermediate metabolites such as hormones and enzymes. (Peters, T et. al.,). Because albumin accounts for approximately 80% of the oncotic pressure of plasma, a 50% reduction in serum albumin concentration consequently produces a 66% decrease in colloid oncotic pressure. (Rainey T. G., et al., 1994). In critically ill patients, risk of death is inversely related to serum albumin concentration. (Cochrane et al., 1998). Goldwaser and Feldman estimate that for each 2.5 g/dL decrease in serum albumin concentration, there is a 24%–56% increase in the risk of death. (Goldwaser et al., 1997). This estimate was made after adjusting for other co-variants (e.g., renal function, serum trans-aminase, lactic acidosis), and it strongly indicates that albumin infusion may have a direct cytoprotective effect. (Cochrane et al., 1998).

Given the above, it is clear that hSA is perhaps the best known of all the plasma proteins judging both by the amount of scientific literature available describing it as well as through the number of industrial uses it enjoys. However, this abundant amount of knowledge is focused primarily on its physiology and the clinical use of albumin, not the methodology used to purify it or sourcing the molecule from anything other than plasma fractionation. The best-known and still widely used purification methods were developed by Cohn and co-workers 60 years ago (Cohn E. J. et al., 1947). The Cohn plasma fractionation method is primarily used to produce purified plasma products for a wide variety of clinical uses. Cohn also developed a widely used crystallization process which utilizes principles similar to those well-known from plasma fractionation processes for use with human serum albumin. However, the process has significant inefficiencies and often does not provide an adequate supply of highly purified hSA.

Effect of pH

The effect of pH is one of the major factors in protein crystallization. Usually protein crystals have a well-defined minimum point of solubility at a specific pH. In the general literature of protein crystallization, it is most often the case that this minimum solubility is at the isoelectric point of the target protein. However, hSA is highly soluble at its isoelectric point, across a wide range of ionic strengths. Thus, the crystallization properties of albumin are much more complex than those of many other proteins making reliable crystallization and/or purification problematic.

Albumin has a varying isoelectric point depending on the chemical treatment that it has received. With a full complement of six bound fatty acids hSA's pI is normally 4.6, however, when fully de-fatted its pI may be as high as 5.6. Therefore, the crystallization properties of hSA vary as between its "native" and de-fatted states and the reported optimum pH for the crystallization of hSA itself varies substantially in the literature from a low of pH 4.6 to a high of pH 8.0 and may be highly dependent upon the molecular state of hSA in a batch-by-batch basis. Thus, the wide range of pH that is considered to be optimal for the crystallization of hSA present in the literature is confusing and apparently relies on various precipitating reagents, each of which is utilized having a variable concentration and which may be optimal for only one of the possible molecular states of hSA.

For example, with hSA at low ionic strength, like that expected in the Cohn alcohol process, crystallization proceeds optimally at pH 4.9–5.3 which is close to the isoelectric point of native albumin. In conditions with a higher ionic strength and when strongly buffered the optimal pH for crystallization by PEG solutions is 7.4. In sum, the reported pH effects for optimal crystallization of hSA are dependent on the reagent composition in such a seemingly irregular way that solid conclusions cannot be made by reference to the prior art and prior art methodology. In fact, given the status of the teachings of the prior art, every new reagent and technique must be laboriously optimized according to a specific pH or other single variable to be kept constant while crystallization conditions are worked out.

Effect of Precipitating Reagents

It should be noted that hSA has a very high solubility in varying salt concentrations. It can be precipitated or crystallized at low ionic strength with added ethanol (Cohn process; Cohn E. J. et al., 1947) or other solvents. Alternatively, salting out with very high salt concentration is possible, and the early literature mostly used ammonium sulfate or ethanol is described. In the more recent literature PEG solutions of various molecular weights have be utilized widely. However, the reagents present in the literature are unacceptable for the clinical use of the resulting hSA because of the remaining contaminants. Of the prior art precipitating reagents only ethanol and ammonium sulfate are useful in the production of has. However, they both have significant practical problems. Crystallization with ethanol requires the addition of toxic organic modifiers such as benzene or heavy metals. Ammonium sulfate is not a suitable salt for final albumin formulation, and would thus need to be removed.

Effect of Specific Reagents

In addition to its other characteristics albumin has an extraordinary capacity to combine and attach to a wide variety of smaller molecules and ions. The association of various long chain alcohols and fatty acids with hSA strongly affect the crystallization profile of molecular hSA and again act to make the production of clinical grade human serum albumin highly variable and unpredictable. Examples of reagents capable of significantly effecting the crystallization profile of hSA include: decanol, palmitic acid and caprylic acid.

Effect of Temperature

In should also be noted that prior art attempts to crystallize hSA in ethanol solutions have typically been made at low temperatures in the range of 0–10° C. High salt and PEG procedures are often made at a wider temperature range of 4–20° C. In these prior art efforts it is not clear what the effect of temperature really is on albumin precipitation. In ethanol the crystal solubility is seemingly lower at low temperature. The effect of temperature is not clearly described in the PEG and salt methods found in the prior art. For production efficiency and commercial viable processes temperature is one of the major factors. Overall, the significance of temperature is not explained or disclosed by the prior art.

Kinetics and Seeding

According to the prior art, the time period needed for the crystallization of albumin in a given reaction to be complete can take up to several days. However, of the prior art methods those employing ethanol may be the most rapid, requiring only 12 to 24 hours to initiate crystallization. Also according to prior art methods the actual crystallization of albumin may not be possible at all without additives including seeding a reaction mixture with crystals formed from a prior reaction. In addition, the methods of crystallization relying on PEG, may or may not utilize this type of additive. It should be noted that seeding does speed up the crystal growth significantly, though given the confusion in the art generally there are no references that can be utilized which give consistently reliable results or generate a high yield of crystal.

TABLE 1

Example List of Crystallizing Reagents and Conditions Found in the Literature.

| Precipitants | Additives | buffers 0.05–0.1 M | pH | temp. ° C. | References |
|---|---|---|---|---|---|
| $(NH_4)_2SO_4$ 50% | Decanol | phosphate | 4.6–7.7 | 4–6 | Haupt, H. and Heide, K. Klin. |
| $Na_2SO_4$ 15–20% | | acetate | 5.0–6.8 | 20 | Wochenschr. (1967), 45(14), |
| K-phosphate 2.2 M | | | 5.9 | 4–6 | pp. 726–729. |
| Na-phosphate 3 M | | | 6.8 | | |
| PEG 180–800 40% | | K-phosphate | 4.6–7.2 | 4 | (1) Carter, D. C. EP 0 357 857 A1 and |
| PEG 400 40% | | Na-acetate | 6.8 | | (2) Carter, D. C. et. al. |
| | | Na-citrate, Tris | 5.5–7.2 | | Science 244 (4909) (1989) p. 1195 |
| PEG 3350 17.5% | long chain fatty acids | phosphates | 7.5 | 22 | (1) Carter, D. C. U.S. 5.585.466 and |
| | | Na-acetate | 4.6–8.0 | | (2) Carter, D. C. et. al. Eur. J. |
| | | Na-citrate, Tris | 7.0–7.5 | | Biochem. 226(3)(1994) p. 1049 |
| PEG 3350 28–30% | | K-phosphate | 7 | 4 | Bhattacharya et al J. Biol. Chem. 275(49)(2000) p. 38731 |
| PEG 400, 4000 20–38% | | K-phosphate | 5.0–5.5 7.0–8.0 | 15–20 | Sugio, S. et. al. Prot. Eng. 12(6) (1999) p. 439 |
| $(NH_4)_2SO_4$ 45% saturated | Decanol | K-phosphate | 6 | 4 | Rao, S. et. al. J. Biol. Chem. 251(10) (1976) p. 3191 |
| MPD | Decanol 0.1% | | 5.2 | 1 | McClure, R. J. et. al. J. Mol. Biol. 83(4) (1974) p. 551 |
| Ethanol | | | 5.2 | 2 | Low, B. W. J. Am. Chem. Soc. 74(1952) p. 4830 |
| $(NH_4)_2SO_4$ 54% saturated. | Decanol 0.2% | | 6.8 | 1 | Low, B. W. and Weichel, E. J. J. Am. Chem. Soc. 73(1951) p. 3911 |
| Methanol | Numerous compounds | acetate | 4.4–6.5 | −5 | Lewin, J. J. A M. Chem. Soc. |
| Ethanol 5–30% | | | 4.9–5.1 | +5 | 73 (1951) p. 3906 |
| Acetone | heavy metals | | | | |
| Ethanol, mole fractions 0.02–0.163 | $CHCl_3$ Decanol, benzene, | | 4.9 5.3 | −5 +10 | Cohn, E. J. et. al. J. Am. Chem. Soc. 69 (1947) p. 1753 |
| Ethanol 15% | Decanol $HgCl_3$ | | 5.2 | <0 | Hughes, W. L. J. Am. Chem. Soc. 69 (1947) p. 1836 |

Prior Art Methodology with Mineral Salts

The prior art (Haupt and Heide (1967)) provided methods to crystallize human serum albumin with various mineral salts including: 50% saturated $(NH_4)_2SO_4$; 15–20% $Na_2SO_4$; 2.2M K-phosphate pH 6.8 and 3M Na-phosphate pH 5.0. Decanol was found to be a necessary crystallization aid in these prior art methods. Other fatty alcohols with more than five carbon atoms in their molecular backbone were found to be useful also. However, the crystallization conditions and procedures were very sparingly described. No material balances were presented. On the basis of the data available from this citation it is not possible to perform crystallization of albumin in a sufficiently controlled or reliable way.

A review of the prior art literature indicates that while there are several methods of crystallization proposed the relevant citations do not teach a process that is efficient at an industrial or commercial scale, teach a method that is unavailable for use in the production of a therapeutic product or excipient, or provide a process only useful in the production of single crystals useful only in x-ray diffraction studies. Thus, the limitations of the prior art prevent the development of the extensive knowledge of crystallizing conditions necessary in the design of a large-scale crystallization processes for hSA in a therapeutic, pharmaceutical excipient, or medical adjuvant role. Moreover, the prior art does not provide teachings that provide for the use from sources other than human plasma. Therefore, a need exists to understand the physical and chemical conditions which produce crystals of albumin reliably and on an commercial scale from a variety of sources.

SUMMARY OF THE INVENTION

The present invention provides improved methods for producing crystalline human albumin. The method is suitable for various albumin sources including: human plasma, and from recombinant albumin sources such as cultured mammalian cells, the milk or other bodily fluids of transgenic mammals, transgenic plants, transgenic avians, recombinant bacterial cell cultures, recombinant yeast cell cultures or recombinant insect cell cultures. That is, it is useful for the production of crystallized and pharmaceutically grade hSA regardless of the feedstream from which it comes. The method has a high purification power so that crystalline albumin can be effectively separated from other proteins, bacteria, fatty acids or other molecular species present in a particular starting material or feedstream. In an additional embodiment of the current invention, albumin can be dissolved and re-crystallized by heating and cooling cycle in the crystallizing medium. This, re-crystallization procedure can be repeated unlimited number of times according the needs of the user of the current invention. Purity of albumin is regularly improved in the re-crystallization procedure.

The methods of the current invention also provide precise combinations of reagents and conditions that allow the optimization of the production of crystalline human albumin. In these methods important the process parameters such as pH and temperature are precisely manipulated. An additional embodiment of the current invention provides optimal concentrations of precipitating agents of sodium or potassium phosphates and/or caprylic acid or caprylate salts.

The process of the current invention is based on certain key factors influencing the crystallization of human albumin. Preferably, the process of the current invention optimizes the following variables in a specific manner so as to optimize the crystallization protocol parameters as follows:

1. changing the phosphate salt concentration in planned steps;
2. varying the temperature of the reaction mixture in planned steps wherein heating and cooling procedures are applied successively;
3. controlling the pH or varying the pH of the reaction mixture planned steps manner;
4. wherein the application of these specific steps allows the purification and crystallization of human albumin from a given feedstream.

Other features and advantages of this invention will become apparent in the following detailed description of preferred embodiments of this invention, taken with reference to the accompanying drawings

DESCRIPTION OF THE PREFERRED EMBODIMENT

The following abbreviations have designated meanings in the specification:

Abbreviation Key:

| | |
|---|---|
| pH | A term used to describe the hydrogen-ion activity of a chemical or compound according to well-known scientific parameters. |
| PEG | An abbreviation for polyethylene glycol |

Explanation of Terms:

| | |
|---|---|
| Colloids | Refers to large molecules that do not pass readily across capillary walls. These compounds exert an oncotic (i.e., they attract fluid) load and are usually administered to restore intravascular volume and improve tissue perfusion. |
| Diafiltration | An operation incorporating ultrafiltration membranes to efficiently remove salts or other small molecules from a macromolecular solution. The purpose is to remove small molecules from albumim in soltuon and adjust the buffer for the next procedure. |
| Tissue Perfusion | The amount of blood flow to tissue. |
| Feedstream | The raw material or raw solution provided for a process or method and containing a protein of interest. |

The methods of the current invention for the crystallization of hSA provide a highly desirable method to separate and purify albumin from a feedstream containing a variety of other protein components. Crystals are the most pure form of protein, once precipitated crystals have significantly better mechanical handling properties than amorphous precipitates and can be separated by a variety of methods known in the field. For example, crystals can be separated and washed efficiently on industrial filters. Crystallization is the most used final purification method of fine chemicals and pharmaceuticals.

According to a preferred embodiment of the current invention albumin is crystallized with a mixture of sodium and potassium phosphates. Crystallization is optimized by using the invented process conditions and methods in a systematic manner. Albumin may precipitate as amorphous phase, liquid droplets or gel if the conditions are not adjusted optimally. Amorphous precipitate is very difficult to handle, it can not be separated and washed efficiently on filters. Amorphous phase does not readily convert to crystals. Crystals production is optimized when the process conditions are adjusted according to this invention. Various embodiments of the current invention are provided below.

1. Phosphate Salts:

Mixtures of sodium and potassium phosphates are preferably used, although crystallization can be made either with sodium phosphate alone or potassium phosphate alone. Phosphate salts $NaH_2PO_4$ and $K_2HPO_4$ are preferred since they can be dissolved in concentrates of up to 4 molar aqueous solutions. These 4 M phosphates can be mixed in all proportions to make 4 M crystallization buffers with various desirable pH values.

Figure 1:
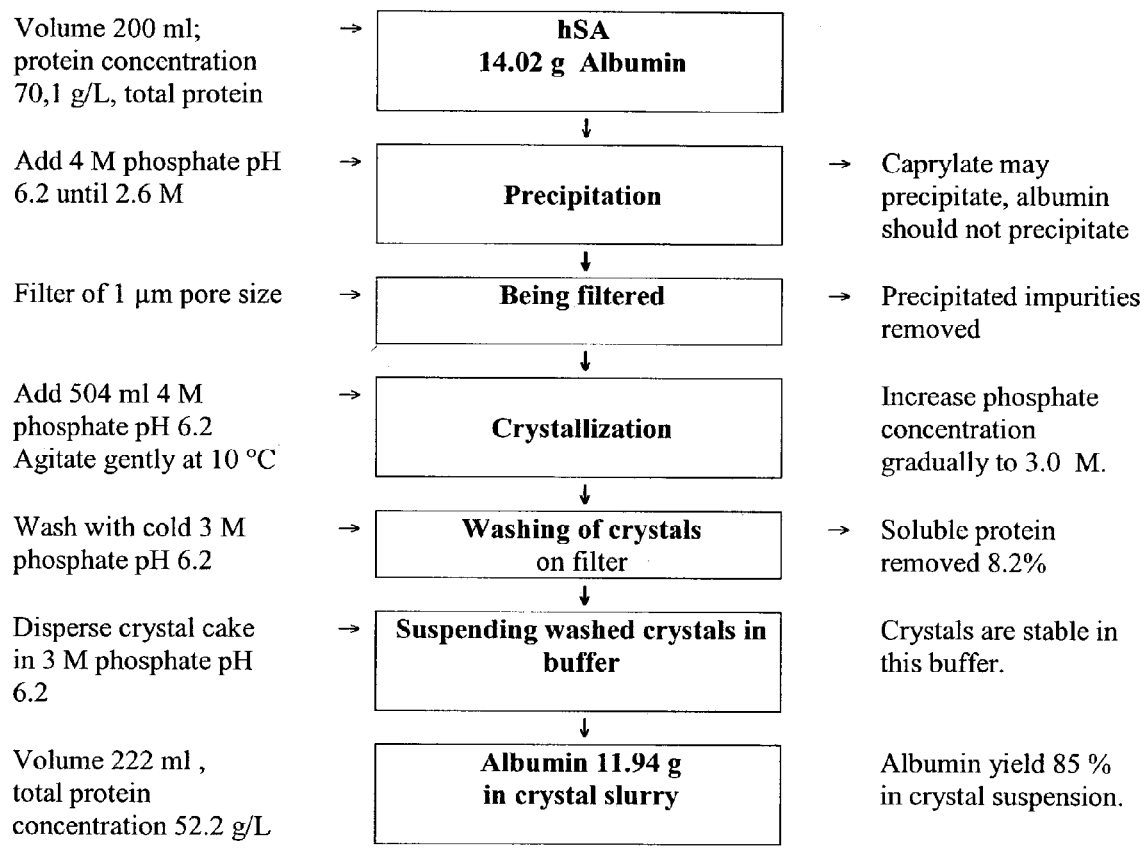
FIG. 1 shows a process flow diagram for crystallization of recombinant human serum albumin.
Figure 2:
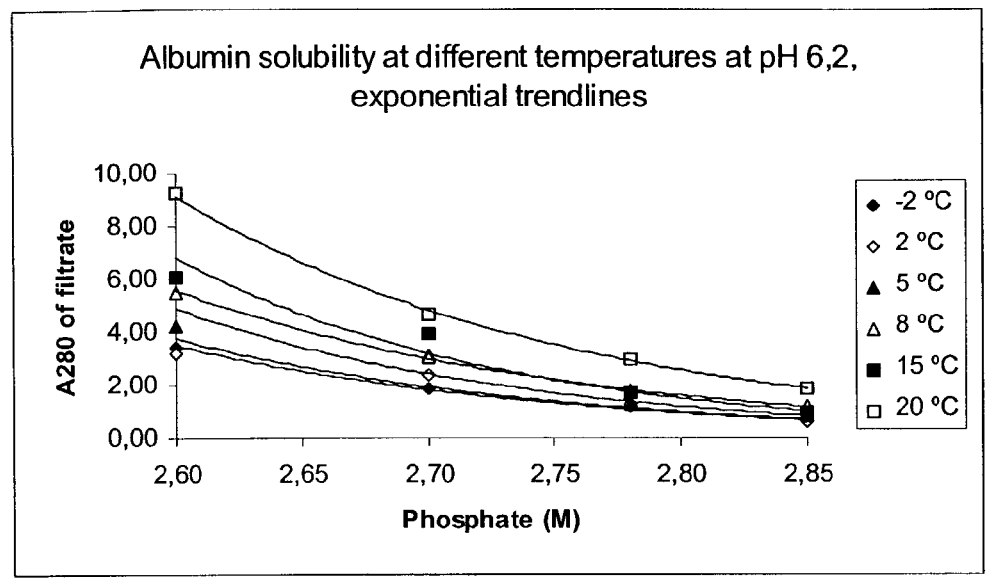
FIG. 2 shows albumin solubility at different temperatures at pH 6.2, with exponential trendlines.

Preferably, albumin is crystallized in relatively high phosphate concentration, typically around 2.7 M or higher. The significance of phosphate concentration is most clearly revealed in the FIGS. 1 and 2, which describe the solubility of albumin crystals in phosphates with different molarities. The semi-logarithmic plot of FIG. 2 shows that crystal solubility is systematically lowered by increasing phosphate molarities. Albumin yield can be adjusted in the process to a desirable level by using increasing molar concentrations of phosphates. Upper limits for usable phosphate concentrations are set by the solubility of phosphate salts. Phosphate solubility is lowered by lowering temperature and increasing albumin concentration. In one embodiment of the current process phosphate solubility is significantly lowered by reducing the temperature of the reagent to below 10° C. By lowering the temperature of the reagent and increasing the albumin concentration the available water concentration is also being lowered.

According to a preferred embodiment of the current invention, most of the impurities precipitate effectively in starting material in the range of phosphate concentration 2.0–2.7 M, where albumin does not readily crystallize at room temperature (25–30° C.). The impurities are removed by being filtered (after adjusting phosphate concentration 2.0–2.7 M). Thereafter the filtrate is refrigerated to 10° C. where albumin is crystallized. Furthermore, phosphate concentration can be increased (utilizing the information of FIGS. 1 and 2) in order to increase albumin yield in the crystals, see also Table 2 and FIG. 4.

2. Significance of pH:

According to the current invention the pH of the crystallizing batch is fully controlled with the phosphate mixture. Examples of the mixtures with various pH values and the resulting effect on the albumin crystals are presented in the Table 1. The effect of pH on the albumin crystal solubility is presented graphically in the FIG. 2, see also Table 2. Albumin crystal solubility is lowered by lowering pH from pH 5.6 to approximately 6.6. The crystal solubility remains at very low level up to at least pH 7.4. Crystals are completely dissolved below pH 5.5.

The pH has a specific effect on the crystallization kinetics, thus the higher pH range 6.3–7.4 can not be used in a simple way. In the higher pH range, albumin precipitates as amorphous (liquid droplet) phase if such pH is adjusted right in the beginning of the process. Thus the crystallization process is preferably made initially with the phosphate pH 6.2 (see table 1 for mixing recipe of phosphates and FIGS. 2 and 3). Later on when albumin is mostly crystallized, phosphate concentration is increased and pH adjusted to higher value in order to increase the crystal yield. Higher pH is also used advantageously when washing crystals, since the loss of albumin is reduced.

3. Effect of Temperature

Figure 3:
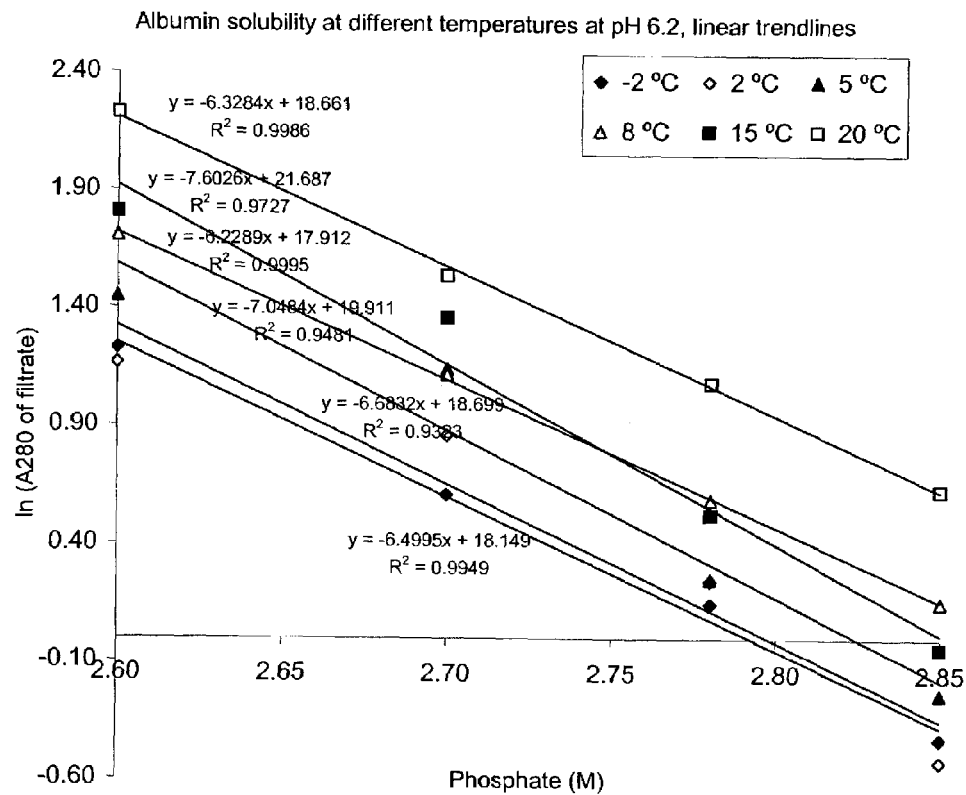
FIG. 3 shows albumin solubility at different temperatures at pH 6.2, with linear trendlines

The solubility of albumin crystals at different temperatures and phosphate concentrations is presented graphically in the FIG. 3. Albumin crystal solubility is increasing at higher temperatures. Lowest solubility is found around 0° C. However, the preferred crystallizing temperature is around 10° C., since at lower temperature phosphate may crystallize and bring the process out of control. The example procedures around 0° C. were possible to be performed, since phosphate crystallization is relatively slow.

The crystallization kinetics of albumin is very slow at room temperature. Thus the phosphate concentration can be adjusted to 2.6–2.7 at room temperature without precipitating or crystallizing albumin. However, impurities are readily precipitated at room temperature. After being filtered, albumin solution is refrigerated to preferably 10° C. The solution is stirred and albumin is crystallized.

Figure 7:
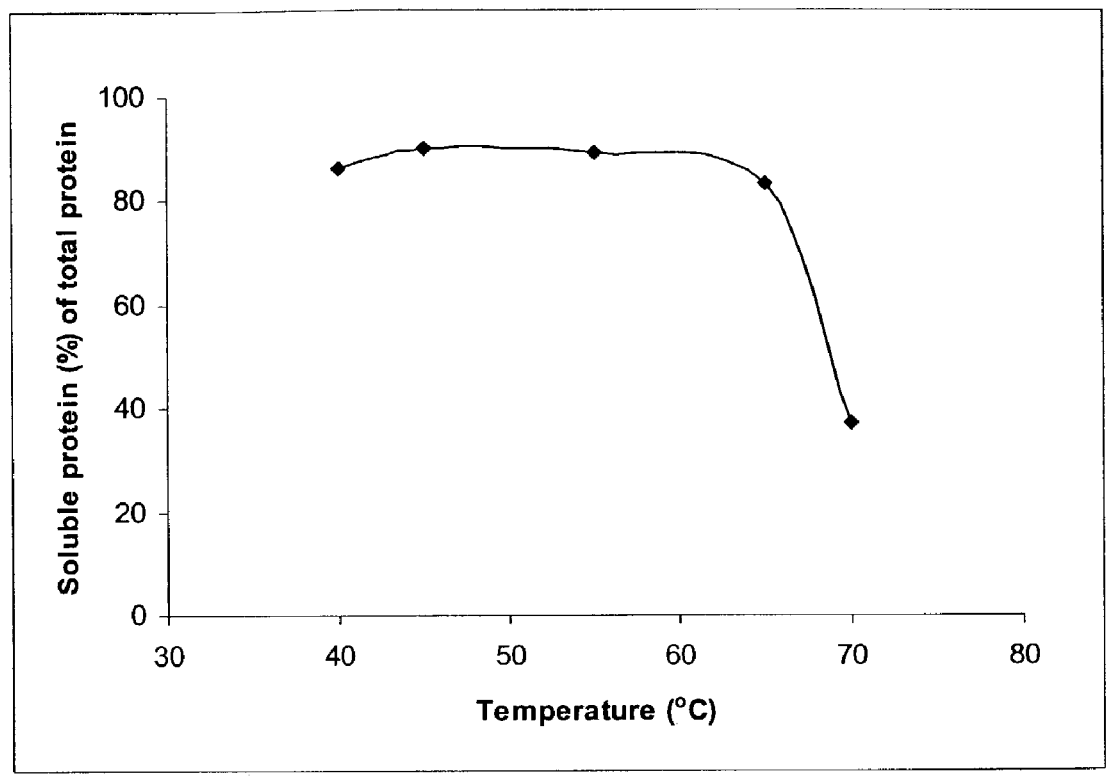
FIG. 7 shows a heat precipitation study of hSA crystal slurry in 2.7 M phosphate pH 6.2.
Figure 8:
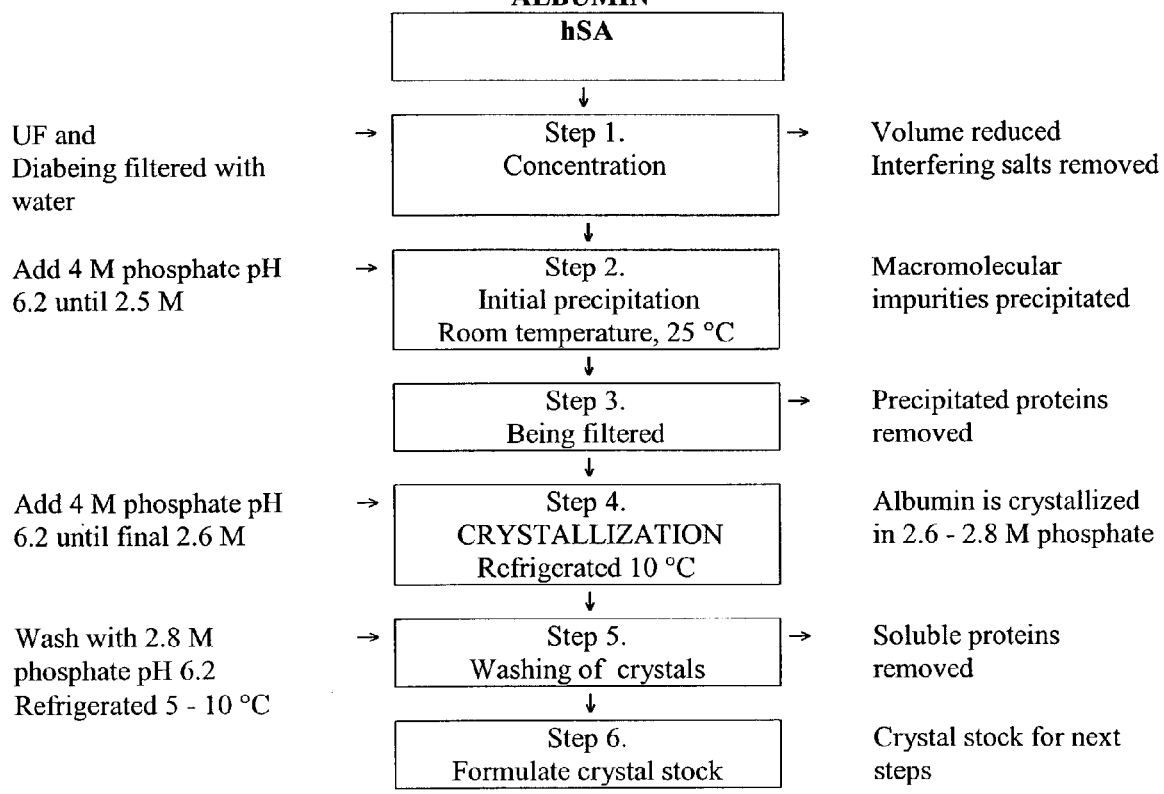
FIG. 8 shows a process flow diagram for preparative crystallization of albumin.
Figure 9:
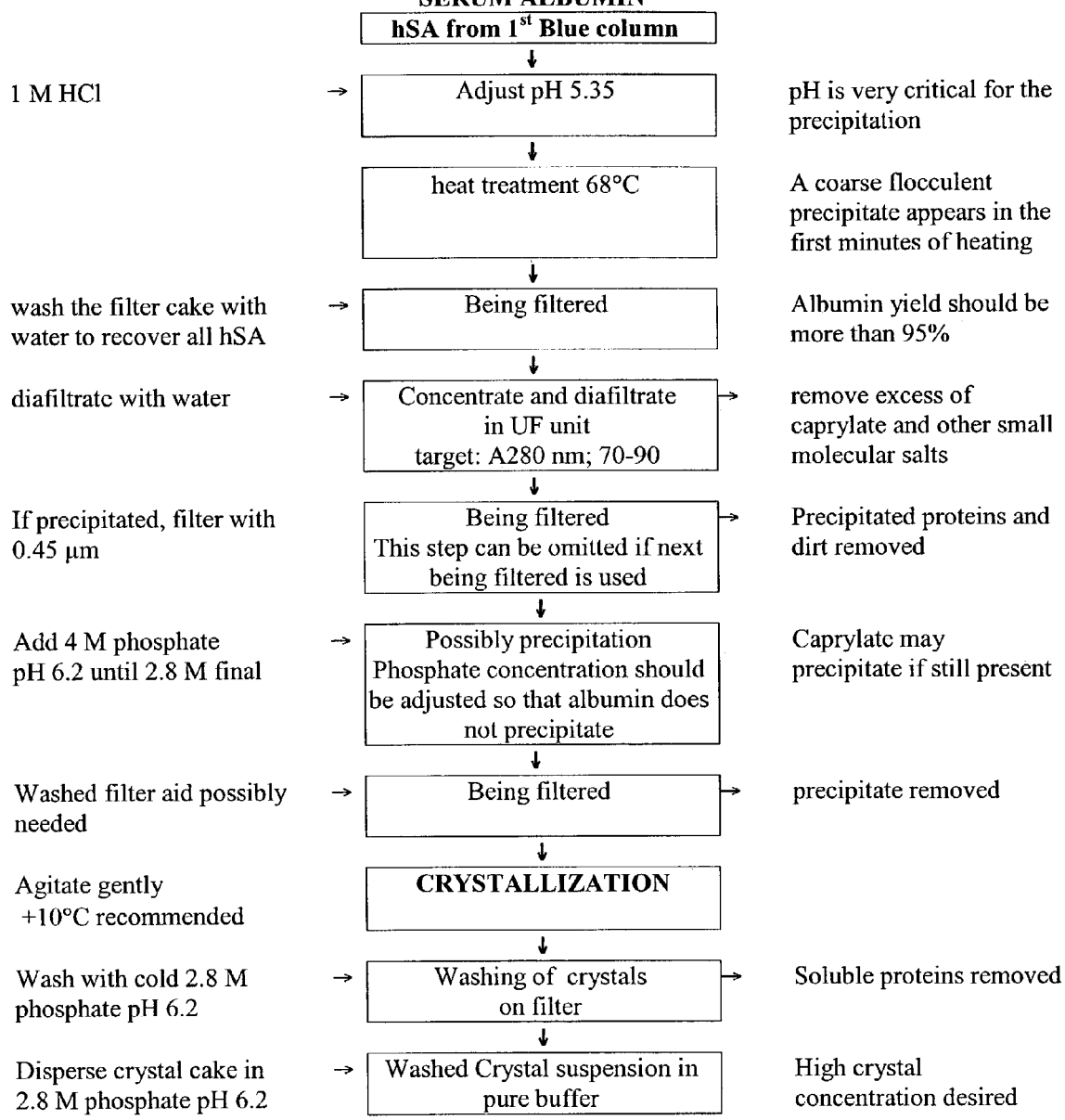
FIG. 9 shows a process flow diagram for crystallization of recombinant human serum albumin.
Figure 10:
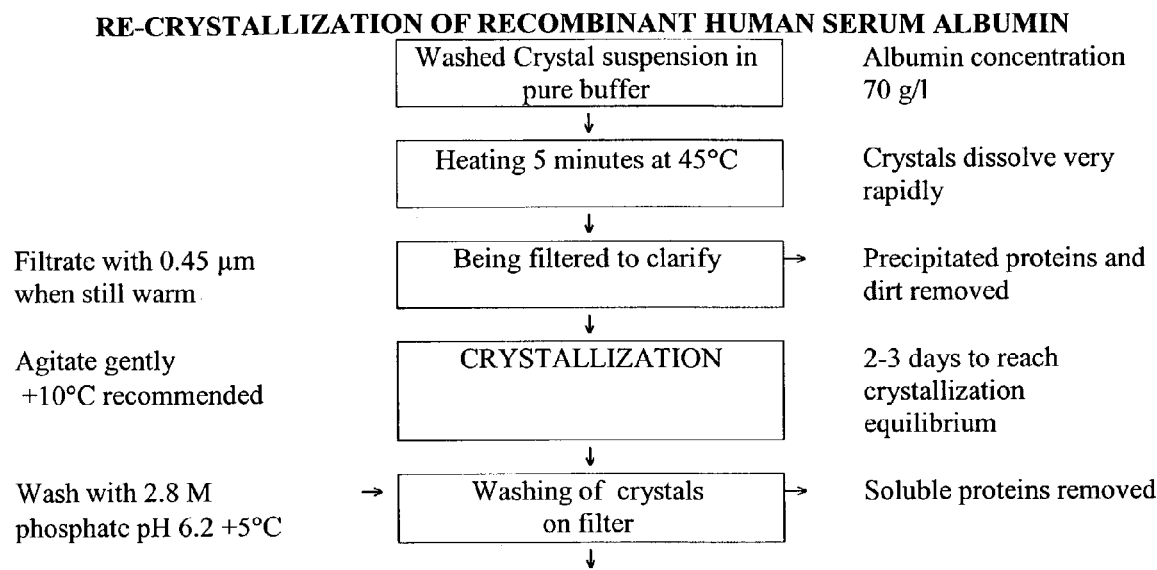
FIG. 10 shows a process flow diagram for the re-crystallization of recombinant human serum albumin.

Albumin can be re-crystallized by utilizing a heating cycle. The crystals are dissolved by heating to 45° C. Albumin is crystallized again after refrigeration to 10° C. Recrystallization can be used to improve the crystal purity. After each crystallization, the mother liquor can be removed by being filtered. Crystals can be washed on the filter with cold 3 M phosphate. Re-crystallization cycle can be repeated unlimited number of times. Re-crystallization can be used to improve albumin purity. For convenience please see Tables 7 and 8 and FIG. 7.

Albumin is relatively heat stable. It can be heated up to 65–70° C. for prolonged periods. Most other proteins denature and precipitate at such high temperatures. Thus heating treatment at 65–70° C. can be used to purify albumin solution prior to crystallization. The highest tolerable temperature is related to the composition and pH of albumin solution. In high phosphate concentration pH 6.2 the highest temperature is 65° C. In low salt medium and pH 5.4 heating at 70° C. for 2–3 hours is possible. Examples of the effect of heat treatment are presented in the Tables 2 and 3 and FIG. 6.

4. Caprylate

Albumin needs to be saturated with caprylate to be able to crystallize. Caprylate has also a stabilizing effect on the albumin, specially on heat stability. Other long chain fatty acids and long chain alcohols are alternatively useful. Decanol is very effective and well known in prior art. Caprylate has dual effect depending of how it is used. It is beneficial when it is used only to saturate the binding sites of albumin. However, excess of caprylate will dissolve crystals and reduce albumin yield.

Figure 4:
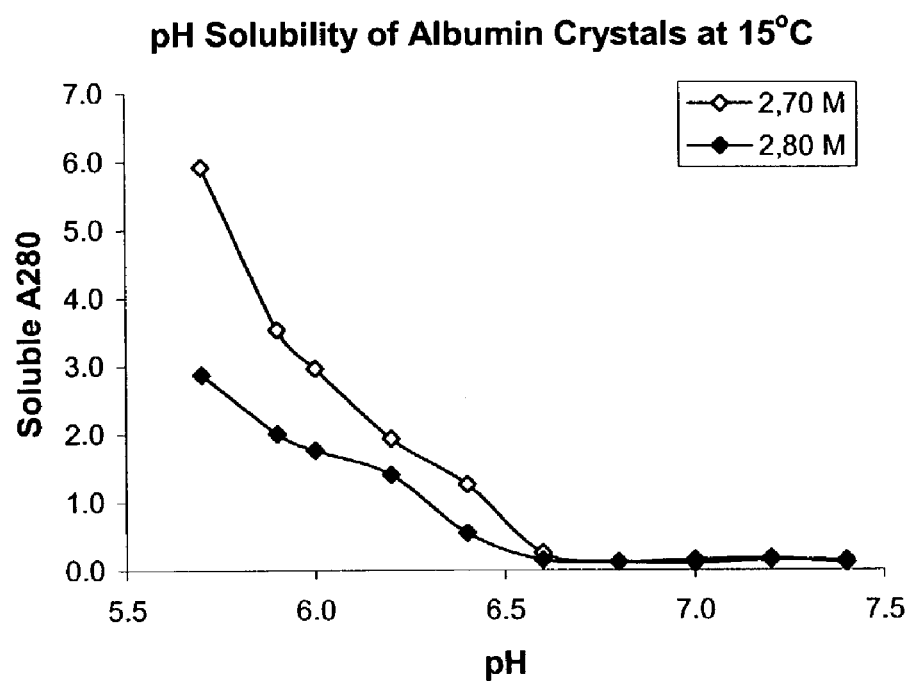
FIG. 4 shows pH Solubility of albumin crystals at 15° C.
Figure 5:
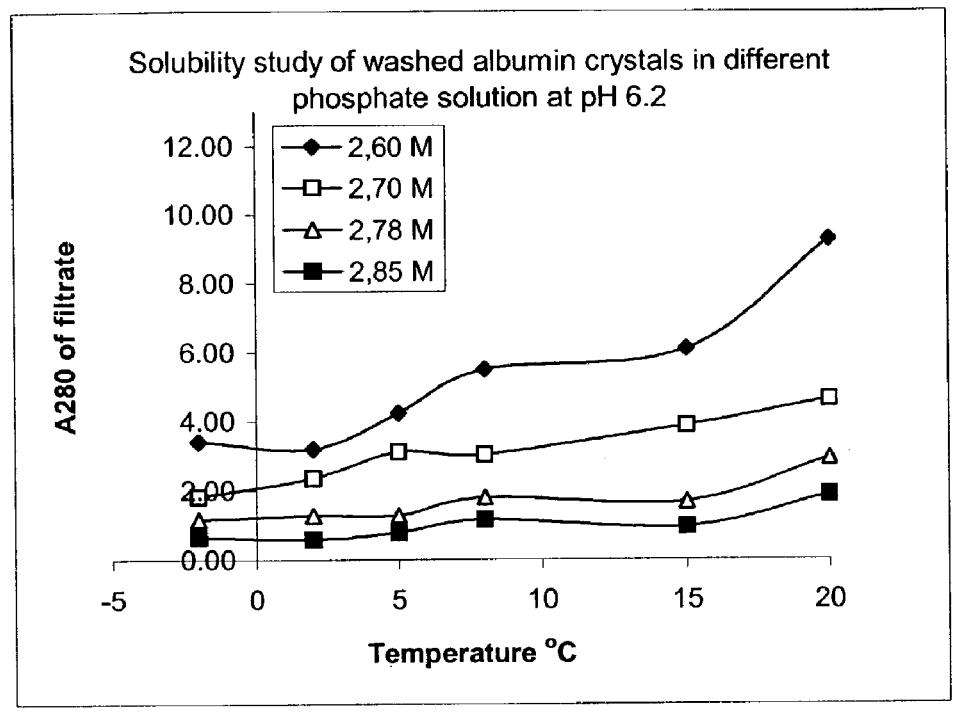
FIG. 5 provides a solubility study of washed albumin crystals in different phosphate solution at a pH of 6.2.

The effect of caprylate is well revealed in the FIG. 4. Addition of caprylate to the washed crystals clearly increased crystal solubility. Crystal solubility was rapidly increasing when caprylate was increasing up to 10 mM. The solubility increment was smaller but still significant when caprylate was increasing from 10 mM to 20 mM. At phosphate concentration 2.63 M and temperature 10° C., albumin solubility increased from 9 mg/ml in 10 mM caprylate to 21 mg/ml in 10 mM caprylate. At higher phosphate concentration 2.82 M and temperature 10° C., albumin solubility increased from 2 mg/ml in 0 mM caprylate to 12 mg/ml in 10 mM caprylate.

Dissolving effect of caprylate is so significant that concentration of free caprylate should be well controlled and maintained as low as possible in the crystallizing step. Small level of free caprylate, order of 1–2 mM may be acceptable when conditions are otherwise such that albumin crystal solubility is very low. Please see FIGS. 2 through 7.

5. Albumin: Concentration, Purity

In experimental solutions albumin concentration in the starting solution is set to a level that is higher than the solubility of crystals in the conditions utilized. According to the current invention, when working with a feedstream sourced from a transgenic animal or cell culture initial clarification steps are typically used to provide a solution in with the concentration of albumin and other chemical parameters are adjusted or manipulated such that it is also higher than the solubility of hSA crystals. In both of these situations albumin recovery can be estimated by using the solubility information in the phase diagrams (FIGS. 1–4). According to the current invention concentration levels of albumin in feedstream solutions are typically in the range of 15–300 grams of albumin in one liter of crystallizing batch. In feedstreams from biological sources and usable for the commercial or industrial production of hSA these same ranges are encountered.

Moreover, albumin need not be pure in the crystallizing process according to the preferred embodiments of the current invention. The processes developed—and provided by the current invention can be utilized to crystallize out albumin in source material wherein the level of purity is approximately 10%, that is, where albumin constitutes only 10% of the total protein of a given solution. For example, with hSA sourced from either transgenic sources or cell cultures most of the impurities remaining after clarification procedures can be removed after precipitation with the first addition of phosphate up to 2.6 M concentration level. It should be noted that transgenic sources, typcially milk, but also including other bodily fluids such as blood or urine may contain hSA as a consequence of the insertion of DNA constructs designed to cause the stable expression of hSA (or other protein of interest) in those bodily fluids or tissues. After the precipitation and being filtered, the filtrate is further concentrated by ultrafiltration in order to increase albumin concentration level. Thereafter the concentrated albumin solution is refrigerated and crystallized according to the current invention.

EXAMPLE 1

A Preferred Crystallization Process

This process description is made for the crystallization of a purified albumin solution and for that purposes describes the use of only a phosphate solution only. However, according to the current invention this method can be used on impure or only partially purified starting material, as may be found from transgenic or cell culture feedstreams, with the addition of additional steps provided herein. Variations of the inventive method, for example utilizing starting solutions with significant impure material, are presented below.

Step 1. Precipitation

Phosphate stock solution, containing 2.8 moles of $NaH_2PO_4$ and 1.2 moles of $K_2HPO_4$ dissolved in water and filled to 1.0 liter, was used in crystallization. This 4 M phosphate solution had pH 6.2 when measured after dilution to 0.5 M. Thereafter, 200 ml of a purified albumin solution was precipitated by adding 371 ml of 4.0M phosphate stock solution at a pH of 6.2. On the basis of the added volume, the phosphate concentration was 2.6 M. The solution was allowed to precipitate at room temperature for 4–18 hours, for this variation of the current invention the time period of interest is short relative to prior art methods, in all cases less than 24 hours. The amount of the produced precipitate is directly related to the amount of impurities in the albumin solution.

Step 2. Filtration

Thereafter, the precipitated hSA was filtered through glass fiber or cellulose fiber paper having approximately 1 µm pore size. The filtered solution was then used in a preferred crystallization procedure according to the invention.

Step 3. Crystallization

Crystallization was performed in 10° C. thermostat incubator. The batch was stirred slowly (approximately 70 rpm) with a top driven propeller. Phosphate concentration was increased gradually from 2.6 M to 3 M by adding 229 ml of 4M phosphate which was at a pH of 6.2. The crystallization batch was continued for a period of 4 days before harvesting and washing.

Step 4. Harvesting and Washing of Crystals

According to a preferred embodiment of the current invention hSA crystals were harvested by filtering the batch with glass fiber paper (1 µm pore size, 142 mm diameter). After being filtered, crystals were then washed with about 80 ml of cold 3 M phosphate pH 6.2. Crystals were then suspended in about 150 ml of cold 3 M phosphate pH 6.2.

Figure 11:
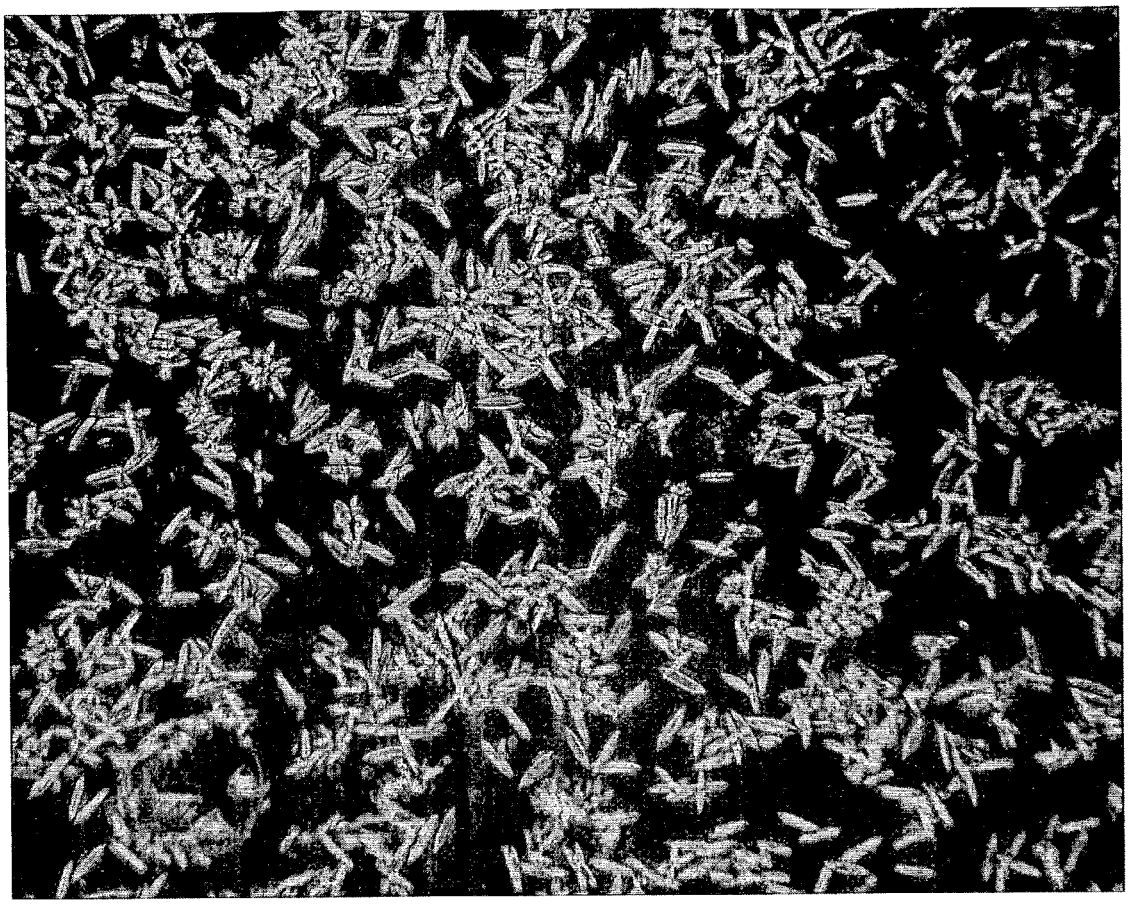
FIG. 11 shows crystallized human albumin in a solution mixture that is 2.3 Molar Na—K-Phosphate with a pH of 6.2; Caprylate 1.4 mg/ml; hSA 80 mg/ml crystallized at 4° C. overnight, with two hours at room temperature (RT) in an air tight chamber.
Figure 12:
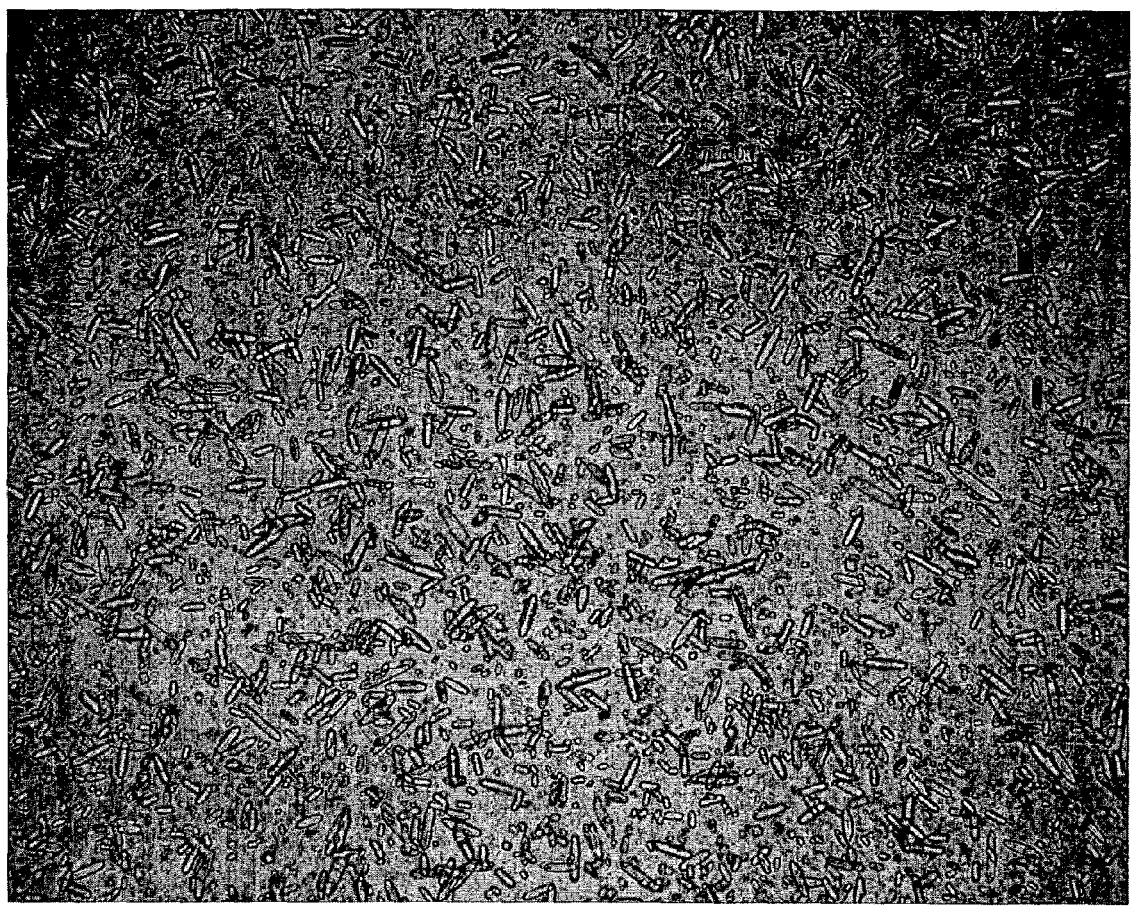
FIG. 12 shows crystallized human albumin shows crystallized human albumin in a solution mixture that is 2.5 Molar Na—K-Phosphate with a pH of 6.2; saturated with Caprylate; hSA 46.5 mg/ml crystallized at 4° C. overnight.

With regard to Table 2 below and the preferred crystallization processes of the current invention, it is preferably if the mixing volume ratios are kept fixed. Preferably, the pH should not be adjusted after making the buffer mixture. For this embodiment of the invention the pH values are approximate, since the value will change with the alteration in phosphate concentration. The buffers of the current invention were used in the study for effect of pH on crystal solubility. As seen below in Table 2, Buffer No: 10 provides conditions that are consistently optimized for crystal development and the conditions provided for this buffer are the preferred conditions for the standard buffer of the current invention. (See also, FIGS. 11–13).

TABLE 2

Mixing Table For 4 M Phosphate Buffers

| Buffer No: | Diluted PH | mixing volumes of 4M A and B | | Behavior of hSA crystals in 2.6–2.8M buffers |
|---|---|---|---|---|
| | | A 4M NaH$_2$PO$_4$ | B 4M K$_2$HPO$_4$ | |
| 1 | 5.3 | 95 | 5 | hSA dissolved |
| 2 | 5.4 | 94 | 6 | hSA dissolved |
| 3 | 5.5 | 92 | 8 | hSA dissolved |
| 4 | 5.6 | 90 | 10 | hSA Crystallized |
| 5 | 5.7 | 87 | 13 | hSA Crystallized |
| 6 | 5.8 | 84 | 16 | hSA Crystallized |
| 7 | 5.9 | 80 | 20 | hSA Crystallized |
| 8 | 6.0 | 77 | 23 | hSA Crystallized |
| 9 | 6.1 | 74 | 26 | hSA Crystallized |
| 10 | 6.2 | 70 | 30 | hSA Crystallized |
| 11 | 6.3 | 65 | 35 | hSA Crystallized |
| 12 | 6.4 | 60 | 40 | hSA Crystallized |
| 13 | 6.5 | 55 | 45 | hSA crystals are stable |
| 14 | 6.6 | 50 | 50 | hSA crystals are stable |
| 15 | 6.7 | 43 | 57 | hSA crystals are stable |
| 16 | 6.8 | 39 | 61 | hSA crystals are stable |
| 17 | 6.9 | 35 | 65 | hSA crystals are stable |
| 18 | 7.0 | 30 | 70 | hSA crystals are stable |
| 19 | 7.1 | 27 | 73 | hSA crystals are stable |
| 20 | 7.2 | 24 | 76 | hSA crystals are stable |
| 21 | 7.3 | 21 | 79 | hSA crystals are stable |
| 22 | 7.4 | 18 | 82 | hSA crystals are stable |

PHOSPHATE BUFFERS
pH values are for diluted buffers in the range of 0.1–0.4 M.
The buffer No: 11. pH 6.3 is not much influenced by dilution.
The buffers No: 1–10 have lower pH when M is higher.
Buffers No: 12–30 have higher pH when molarities are higher.

Figure 6:
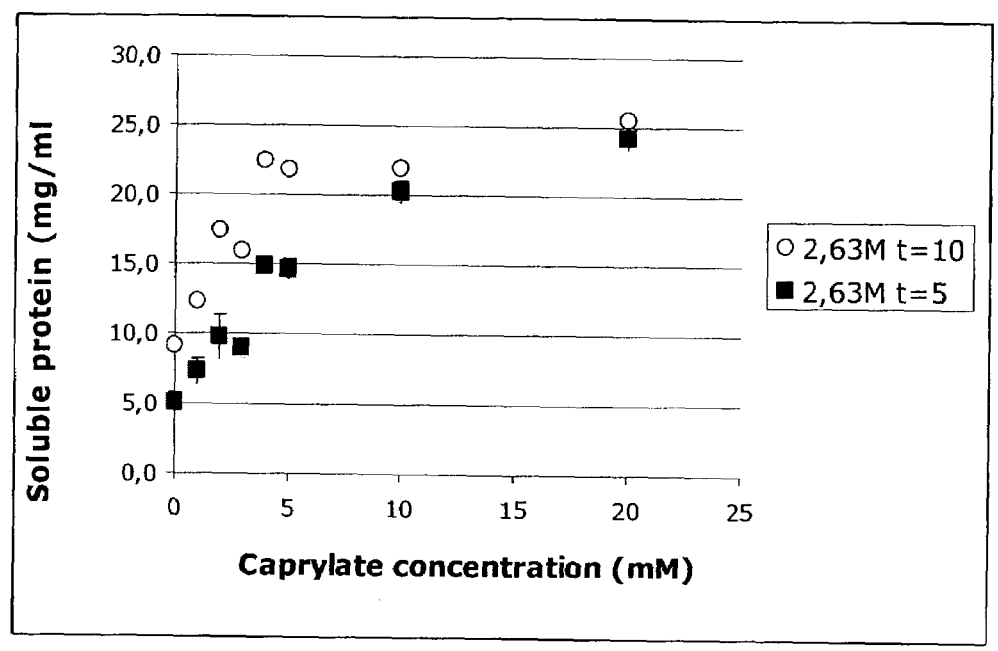
FIG. 6 provides a solubility study of washed albumin crystals in a 2.63M phosphate solution with varying caprylate concentration.

It should also be noted that in FIG. 6 of the current disclosure provides a profile of albumin solubility in 2.63 M phosphate as a function of caprylate concentration and temperature: open circles (○) mark samples incubated at 10° C. and black squares (■) mark incubated at 5° C.

EXAMPLE 2

Crystallization of Albumin with the Microdiffusion Method

Crystallization examples from 48 samples were prepared according to a hanging drop microdiffusion method known in the art. The sample solution contained purified 198 mg/ml of albumin and 3.2 mg/ml sodium caprylate. The liquid solution of albumin was prepared by mixing 3 μl of albumin solution with 3 μl of 1.8–2.3 M phosphate. The drops were allowed to equilibrate in the closed microdiffusion wells and refrigerated at 5° C. Crystals were produced in less than 24 hours according to this embodiment of the the current invention. According to the current invention, feedstreams from other source material, especially transgenic and cell culture sources, can also be utilized in conjunction with a microdiffusion hanging drop method.

The crystals were observed with microscope and photographed with digital camera. Information regarding the development of the crystals are provided on tables 19 and 20. These examples show that caprylate saturated albumin is crystallized in 1.8 M through 2.3 M phosphates in a sharply defined pH range, that is, from 5.0–6.4. The most preferred pH for crystal formation was at pH 6.2, as seen below in Table 3. The range of experimental conditions provided effectively covers the range of concentrations and solution parameters that have been seen in alternate feedstream sources, see Table 4.

TABLE 3

| Sample: | Microscopy Observations |
|---|---|
| Mix 90 μl hSA concentrate 210 mg/ml and 10 μl caprylate solution (32 mg/ml pH 7.3.). Final caprylate concentration is 3.2 mg/ml. | C = crystals |
| | A = amorphous precipitate |
| Drop: 3 μl sample + 3 μl reagent | L = liquid phase separation, spherical droplets |
| Temperature 5° C. | d = days |
| Initial protein concentration: 95 mg/ml | G = gel, glassy solid irregular particles |
| Final protein concentration: 198 mg/ml | N = no phase separations, clear solution |
| | X = experiment failed, discontinued, dried, microbial contamination etc. |

| | | Number of days (d), temperature (° C.) | | | |
|---|---|---|---|---|---|
| well | Reagents: | 1 d, 5° C. | 3 d, 5° C. | 8 d, 5° C. | 18 d, 5° C. |
| A1 | 1.8 M Na—K-phosphate pH 5.0 | L | L | C, G | A, G |
| A2 | 1.8 M Na—K-phosphate pH 5.6 | L | L | C, L, A | C, L, G |
| A3 | 1.8 M Na—K-phosphate pH 6.2 | L | C | C | C, G |
| A4 | 1.8 M Na—K-phosphate pH 7.0 | L, G | L, G | L, G | G |
| A5 | 1.8 M Na—K-phosphate pH 7.4 | G | G | G | G |
| A6 | 1.8 M Na—K-phosphate pH 8.2 | G | G | G | G |
| B1 | 2.0 M Na—K-phosphate pH 5.0 | L | L | G | A, G |
| B2 | 2.0 M Na—K-phosphate pH 5.6 | L, A | L, A | L, G | A, G |
| B3 | 2.0 M Na—K-phosphate pH 6.2 | L, C | C | C, G | C, G |
| B4 | 2.0 M Na—K-phosphate pH 7.0 | A, G | A, G | G | G |
| B5 | 2.0 M Na—K-phosphate pH 7.4 | A, G | A, G | G | G |
| B6 | 2.0 M Na—K-phosphate pH 8.2 | A, G | A, G | G | G |
| C1 | 2.2 M Na—K-phosphate pH 5.0 | L, A | L, A | L, A | A, G |
| C2 | 2.2 M Na—K-phosphate pH 5.6 | L, A | L, A | L, A | A, G |
| C3 | 2.2 M Na—K-phosphate pH 6.2 | L, C | C | C | C, G |
| C4 | 2.2 M Na—K-phosphate pH 7.0 | A, G | A, G | G | G |
| C5 | 2.2 M Na—K-phosphate pH 7.4 | A, G | A, G | G | G |

TABLE 3-continued

| | | | | | |
|---|---|---|---|---|---|
| C6 | 2.2 M Na—K-phosphate pH 8.2 | A, G | A, G | G | G |
| D1 | 2.3 M Na—K-phosphate pH 5.0 | L, A | L, A | L, A | A, G |
| D2 | 2.3 M Na—K-phosphate pH 5.6 | L | L | L | A, G |
| D3 | 2.3 M Na—K-phosphate pH 6.2 | L, C | C | C | C, G |
| D4 | 2.3 M Na—K-phosphate pH 7.0 | A, G | A, G | G | G |
| D5 | 2.3 M Na—K-phosphate pH 7.4 | A, G | A, G | G | G |
| D6 | 2.3 M Na—K-phosphate pH 8.2 | A, G | A, G | G | G |

TABLE 4

Box code: MCSA35
Sample: GTC hSA: 7F 4AC, concentrated using dialysis against PEG 20 k. Mix 45 µl hSA concentrate, 45 ml water and 10 µl caprylate solution (32 mg/ml pH 7.3.). Final caprylate concentration is 3.2 mg/ml.
Drop: 3 µl sample + 3 µl reagent
Temperature 5° C.
Initial protein concentration: 49 mg/ml
Final protein concentration: 98 mg/ml Microscopy observations
C = crystals
A = amorphous precipitate
L = liquid phase separation, spherical droplets
d = days
G = gel, glassy solid irregular particles
N = no phase separations, clear solution
X = experiment failed, discontinued, dried, microbial contamination etc.

| | | Number of days (d), temperature (° C.) | | | |
|---|---|---|---|---|---|
| well | Reagents: | 1 d, +5 C. | 2 d, +5 C. | 3 d, +5 C. | 13 d, +5 C. |
| A1 | 1.8 M Na—K-phosphate pH 5.9 | L | C, L | C, L | C, G |
| A2 | 1.8 M Na—K-phosphate pH 6.0–6.1 | L | C, L | C, L | C, G |
| A3 | 1.8 M Na—K-phosphate pH 6.2 | L | C, L | C, L, G | C, G |
| A4 | 1.8 M Na—K-phosphate pH 6.3–6.4 | L | C, L | L, C | C, G |
| A5 | 1.8 M Na—K-phosphate pH 6.4–6.5 | L | L | L | C, G |
| A6 | 1.8 M Na—K-phosphate pH 6.6 | L | L, A | L | G |
| B1 | 2.0 M Na—K-phosphate pH 5.9 | L | C, L | C, L | C, G |
| B2 | 2.0 M Na—K-phosphate pH 6.0–6.1 | L | C, L, A | C, L, G | C, G |
| B3 | 2.0 M Na—K-phosphate pH 6.2 | L | C, L, G | C, LG | C, G |
| B4 | 2.0 M Na—K-phosphate pH 6.3–6.4 | L | L, G | L, G | G |
| B5 | 2.0 M Na—K-phosphate pH 6.4–6.5 | L | L, G | L, G | G |
| B6 | 2.0 M Na—K-phosphate pH 6.6 | L | L, G | L, G | G |
| C1 | 2.2 M Na—K-phosphate pH 5.9 | L | C, L, A | C, L, A | C, G |
| C2 | 2.2 M Na—K-phosphate pH 6.0–6.1 | L | C, L, G | C, L, G | C, G |
| C3 | 2.2 M Na—K-phosphate pH 6.2 | L, C | C, L, G | C, L, G | C, G |
| C4 | 2.2 M Na—K-phosphate pH 6.3–6.4 | L | L, G, C | C, L, G, | G |
| C5 | 2.2 M Na—K-phosphate pH 6.4–6.5 | L | L, G | L, G | G |
| C6 | 2.2 M Na—K-phosphate pH 6.6 | L | L, G | L, G | G |
| D1 | 2.3 M Na—K-phosphate pH 5.9 | L | C, L, A | C, L, A | C, G |
| D2 | 2.3 M Na—K-phosphate pH 6.0–6.1 | L, C | C, LG | C, L, G | C, G |
| D3 | 2.3 M Na—K-phosphate pH 6.2 | L, C | C, LG | C, L, G | C, G |
| D4 | 2.3 M Na—K-phosphate pH 6.3–6.4 | L | C, L, G, | C, L, G, | G |
| D5 | 2.3 M Na—K-phosphate pH 6.4–6.5 | L | L, G | L, G | G |
| D6 | 2.3 M Na—K-phosphate pH 6.6 | L, G | L, G | L, G | G |

EXAMPLE 3

Crystallization of Albumin in Impure Starting Material

The following process description is originally made from a recombinant hSA starting material which contains much of impurities which interfere the crystallization. The first process steps are needed for removal of impurities. If more pure albumin is used, the number of steps is correspondingly reduced.

Step 1. Concentration

The starting material should be concentrated by ultrafiltration filtered as much as possible. High protein concentration will reduce the usage of phosphate and increase the yield of crystallizable rhSA. The material should also be filtered with water in the end of concentration procedure in order to reduce the salts originating from the previous process steps. Guideline for protein concentration: $A280_{nm}$=150–200.

Step 2. Initial Precipitation with Phosphate

Add 2.5 volumes of 4 M phosphate (pH 6.2) into 1.5 volumes of rhSA concentrate. The final phosphate concentration at this step is 2.5 M which precipitates impurities but not albumin. This procedure is preferably performed at room temperature.

Step 3. Filtration

Remove the precipitate that is filtered out with a Buchner funnel or pressure chamber filter. Diatomaceous earth is used as filter aid, since the precipitate is very finely grained amorphous material. Centrifugation is not a convenient option since the precipitate will float on the top of the liquid.

Step 4. Crystallization

Crystallization of hSA is started by adding more of 4 M phosphate (pH 6.2) in the filtrate until concentration is 2.8 M. Crystallization is performed at refrigerated temperatures preferably around 5.0° C. Crystallization of the hSA, according to this embodiment of the current invention starts spontaneously within 24 hours. In an alternate embodiment the addition of seed crystals will make the process more rapid.

Step 5. Washing of Crystals

According to the preferred embodiment of the current invention crystals are washed either by centrifugation or preferably by being filtered. In centrifugation the crystals float on the top of phosphate buffer. Washing is performed with fresh 2.8 M phosphate solution at temperature around +5° C. Crystal washing should be made with low pressure difference, less than 0.1 bar. The washing is repeated 3–4 times until the soluble protein of filtrate remains at nearly constant low level, $A280_{nm}$=1.0 or less.

Step 6. Formulation of Crystal Stock

The washed crystals are dispersed in a small volume of the 2.8 M phosphate buffer. Crystals can be stored in this until formulated for the next step.

EXAMPLE 4

Crystallization of Impure Albumin after Heat Treatment

Starting Material

The feedstream material used for this example had had a significant amount of proteins as impurities. Albumin was approximately 30% of the protein present. As already stated this is within the typical range of feedstream materials supplied from clarified or partially purified transgenic or cell culture sources. The solutions used included 107 ml of 4 M phosphate pH 6.2 was added into 200 ml of starting material solution (which was in 2 M phosphate before this step) to get 2.70 M solution. According to the current invention this precipitated solution was used as starting solution for crystallization.

Heat Treatment

The precipitated starting solution (in 2.70 M phosphate) was incubated at 55° C. for 90 minutes. A substantial amount of rod-like crystals were formed along with an amorphous precipitate as a result of this heat treatment. Approximately 75% to 80% of total protein was crystallized or precipitated. The crystals and precipitate were removed by filtering the slurry through glass fiber filter when it was still hot. Some diatomaceous earth was used as a filter aid. Only the supernatant filtrate containing albumin was taken for the next step.

Concentration and Filtration

After being filtered, the solution had too low albumin concentration for crystallization. Thus it was concentrated and diafiltrated at 55° C. with a Fresenius Polysulfone UF 6.2 Hemoflow F5HPS dialysis cartridge. The detailed data of process steps is shown in the table 6.

hSA Crystallization

Phosphate concentration of the concentrate solution was increased and adjusted slowly to 2.8. At the same time the batch was gently agitated in a refrigerator in order to crystallize hSA.

The hSA crystals were harvested and washed by vacuum being filtered. Washing solution was 2.88 M phosphate pH 6.4. Heat crystallization of impurities is technically easy and rapid method to remove major impurities of the starting material solution as shown in table 5 below and in FIG. 7.

TABLE 5

Purity Analysis of the Starting Material and Washed Crystals. Results of ELISA Assays.

| ELISA assay | Impure Starting Material | Washed Crystal Samples 101–98 |
| --- | --- | --- |
| BSA (ppm) | 85000 | 14300 |
| β-lactoglobulin (ppm) | 3488000 | 4500 |
| α-lactalbumin (ppm) | 143000 | >100 |
| IgG (ppm) | 69000 | >1700 |

Starting material: Genzyme Transgenics hSA: albumin concentrate lot # X1131FF, protein concentration assays: TP 84 g/l and 79 g/l, ALB 28.58 g/l and 28.75 g/l.

TABLE 6

Impure Albumin from Starting Material to Crystals.

| Batch number and procedure | Composition of the solution, notes | Volume (ml) | Total prot: A 280 × volume | Protein % of starting material |
| --- | --- | --- | --- | --- |
| Start with a lot of product | starting material from Sigma | 200 | 14750 | 100 |
| Concentrate, diafiltrate | | | | |
| Add 4 M phosphate pH 6.2 | Phosphate 2.7 M | 307 | 14736 | 43.7 |
| Heat 90 minutes at 55° C. | strongly precipitated, mostly crystalline | 307 | 14736 | 43.7 |
| Add filter aid and filtrate while hot | clear filtrate | 260 | 3276 | 22 |
| Concentrate with ultrafiltration | clear concentrate, 1.9 M phosphate | 111 | 3024 | 20 |
| Add 4 M phosphate gradually, concentrate | Phosphate 2.8 M | 90.8 | 3024 | 20 |
| Protein in the filtrate | 0.45 μm filtrate of the crystal slurry | 90.8 | 1843 | 10 |
| Protein in the crystals | crystals calculated by difference of A280 nm 33.3–20.3 | 90.8 | 1180 | 8 |

Material balance of the whole sequence of steps was calculated using the 200 ml aliquot of the sample solution.

EXAMPLE 5

Recrystallization of Albumin by using Heating and Cooling Cycles

Previously made hSA crystal slurry in 2.7 M phosphate pH 6.2 with a protein concentration of 37.5 g/l was used as starting material for this study conducted according to a preferred embodiment of the current invention. Five samples of the crystal slurry, 0.50 ml each, were incubated alternatively at 40, 45, 55, 65 or 70° C. for 60 minutes. Crystals were dissolved in all the tested temperatures. At the end of heating, the samples were filtered through 0.45 μm filter. Soluble protein of the filtrates was determined by measuring absorbance at 280 nm.

Figure 13:
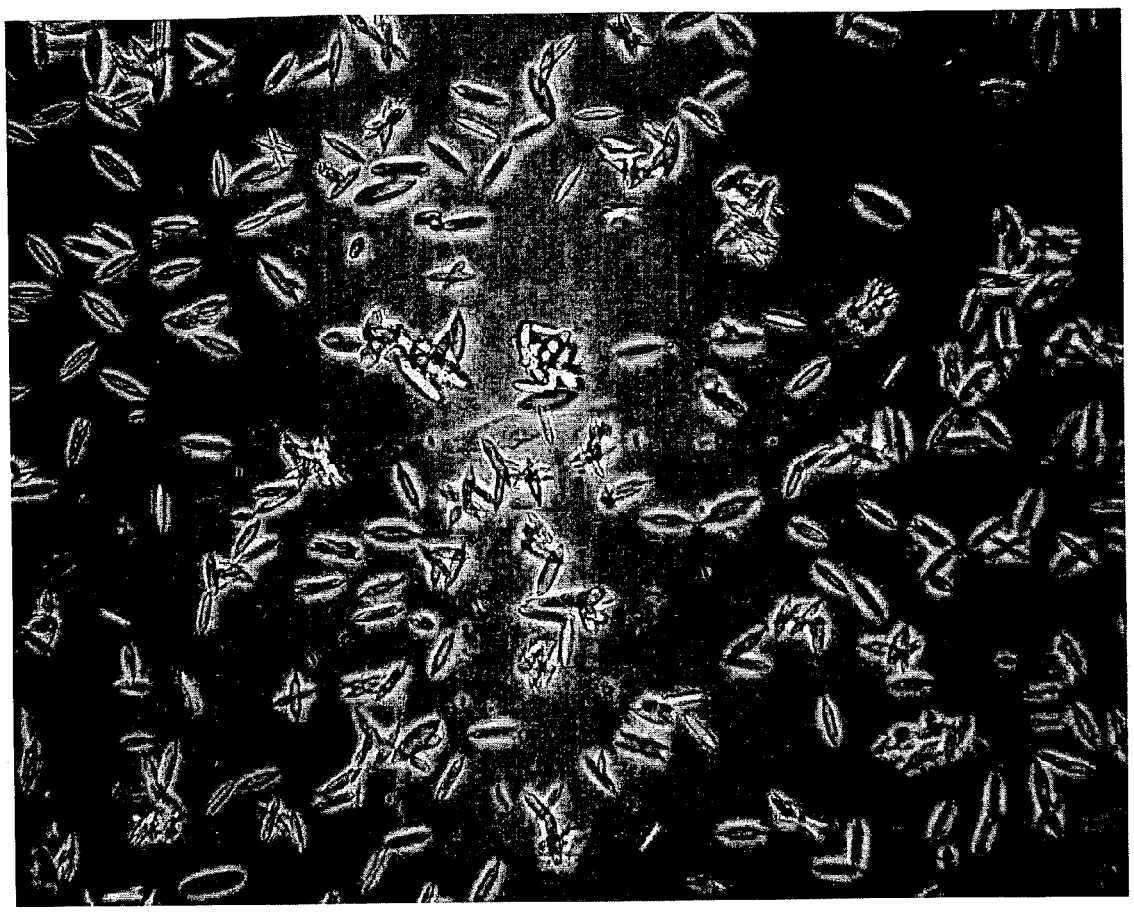
FIG. 13 shows crystallized human albumin in a solution mixture that is 2.3 Molar Na—K-Phosphate with a pH of 6.2; Caprylate 1.4 mg/ml; hSA 80 mg/ml crystallized at 4° C. overnight, with 0 hours at room temperature (RT) in an air tight chamber.

Approximately 10% of total protein was precipitated when the crystal slurry was incubated at 40–55° C. for an hour as seen in tables 7 and 8 and in FIG. 13. This value was rather constant in this temperature range and it represents impurities which were removed in the heating being filtered procedure. When the temperature was increased from 65 to 70° C., the soluble protein of the sample was decreased from 83% to 37%. Thus, also albumin starts to precipitate irreversibly at 70° C.

After being filtered, samples 1 through 5 were heated up to 65° C. were all well recrystallized after 18 hours in refrigerator set at 5° C. When the sample 5 was incubated at 70° C., no crystals were produced in the filtrate, which indicates that albumin is not stable at that temperature in 2.7 M phosphate, see Table 8. These examples show that albumin can, according to a preferred embodiment of the current invention, be well purified by using heating up to 65° C. and thereafter being filtered and going through appropriate re-crystallization cycles.

TABLE 7

Results of the Heat Precipitation Study of hSA Crystal Slurry

| Sample No: | Heated at | Observation after heat treatment, before being filtered | A 280 of filtrate 0.45 μm | Soluble protein (%) of total |
|---|---|---|---|---|
| 1 | 40° C. | Slightly turbid solution. Most of the crystals were dissolved | 17.08 | 86 |
| 2 | 45° C. | Slightly turbid solution, no crystals. | 17.90 | 90 |
| 3 | 55° C. | Slightly turbid solution, no crystals. | 17.70 | 89 |
| 4 | 65° C. | Increasingly turbid solution, no crystals. | 16.60 | 83 |
| 5 | 70° C. | Strongly precipitated slurry, no crystals. | 7.42 | 37 |

TABLE 8

Observations of the heated and filtered samples, re-crystallized at low temperature.

| Filtrate of example No: | Heated at | Microscopy observations after crystallization in refrigerator |
|---|---|---|
| 1 | 40° C. | Well formed crystals |
| 2 | 45° C. | Different sizes, large and very small crystals |
| 3 | 55° C. | Large crystals and crystal clusters |
| 4 | 65° C. | Crystals and crystal clusters |
| 5 | 70° C. | Clear solution, no crystals |

EXAMPLE 6

Crystallization of Albumin at Higher Ph

The studies done according to the current invention show that albumin crystal solubility and crystallization may be dependent on pH. Another issue is the separation of caprylate in the presence of phosphate buffer. The solubility of caprylate increases at higher pH. Thus, even slightly higher pH would be desirable for optimal crystallization formation. According to the current invention, trial crystallizations were made at a range of pH 6.2–6.6 with three different levels of phosphate molarity. Experimental details are presented in the table 9 below.

Evaluation of Results

As seen in Table 9 below, albumin was crystallized very effectively when pH was increased to the values 6.4 and 6.5. Albumin solubility was very low above pH 6.4. Unfortunately, at the higher pH levels albumin was crystallized as very small needles (See FIGS. 10–13). It is likely that the crystal size could be developed larger by starting the crystallization at lower pH 6.2 or 6.3. After achieving near equilibrium, pH could be adjusted to higher level by gradually adding 4M $K_2HPO_4$.

TABLE 9

Test tube crystallization of albumin concentrate 102-5.

| Sample No#. 3 ml each exp. | Soluble protein 20 h (nd = not determined) A280 nm | phosphate M | pH | Microscopy observation N = no phase separation A = amorphous precipitate C = crystals L = liquid phase separation G = gel particle separation |
|---|---|---|---|---|
| RhSA 31 mg/ml | | | | |
| 102-9-1 | nd | 2.46 | 6.2 | N |
| 102-9-2 | nd | 2.46 | 6.3 | N |
| 102-9-3 | 17.6 | 2.46 | 6.4 | Initially L, finally C |
| 102-9-4 | 6.2 | 2.46 | 6.5 | L, C, very thin needles |
| 102-9-5 | 1.5 | 2.46 | 6.6 | C, very thin needles, A |
| 102-9-6 | nd | 2.57 | 6.2 | Intially L, finally C |
| 102-9-7 | 16.2 | 2.57 | 6.3 | Initially L, G, finally C |
| 102-9-8 | 9.0 | 2.57 | 6.4 | L, G, C needles, |
| 102-9-9 | 0.3 | 2.57 | 6.5 | C, short needles or rods |
| 102-9-10 | nd | 2.57 | 6.6 | C, short needles or rods |
| 102-9-11 | nd | 2.67 | 6.2 | Initially G, finally C |
| 102-9-12 | 14.9 | 2.67 | 6.3 | Initially L, G, finally C |
| 102-9-13 | 0.3 | 2.67 | 6.4 | C, many very small needles |
| 102-9-14 | nd | 2.67 | 6.5 | C, many very small needles |
| 102-9-15 | nd | 2.67 | 6.6 | C, many very small needles |

EXAMPLE 7

Re-Crystallization and Washing of Albumin Crystals

Re-Crystallization and Washing

The washed crystals (102–12) were heated 5 minutes at 45° C. The crystals dissolved rapidly. The solution was filtered with 0.45 μm syringe filter while still warm. The filtered solution was agitated at 2° C. until crystallized (3 days). The batch was crystallized well (FIG. 2). The crystals were harvested by being filtered and washed with 2.82 M pH 6.2 phosphate on a 0.45 μm (50 mm diameter) Sartorius membrane. The washed crystals were dispersed in 2.82 M phosphate buffer.

TABLE 10

Recrystallization and Washing of Albumin Crystals

| Step | Ml | A 280 nm | albumin g |
|---|---|---|---|
| Start with 102-12 | 26.9 | 36.9 | 1.877 |
| Step 1. heat 5 minutes at 45° C. | 26.9 | | |
| Step 2. filtrate 0.45 μm | 26 | | |
| Step 3. agitated at 2° C. 3 days (see: FIG. 2) | 26 | | |
| Step 4. Harvest and wash, filtrates | 37.8 | 3.6 | 0.256 |
| Crystal suspension in 2.82 M | 22.1 | 34.8 | 1.451 |
| Sample 102-13 to Sigma 7 | 18 | 34.8 | 1.182 |

Indications and Uses

Hypovolemia

Hypovolemia is a possible indication for albumin purified and made available by the method of the current invention, 25% Solution, Buminate 25%. Its effectiveness in reversing hypovolemia depends largely upon its ability to draw interstitial fluid into the circulation. It is most effective with patients who are well hydrated. When hypovolemia is long standing and hypoalbuminemia exists accompanied by adequate hydration or edema, 25% albumin is preferable to 5% protein solutions. However, in the absence of adequate or excessive hydration, 5% protein solutions should be used or 25% albumin should be diluted with crystalloid. Although crystalloid solutions and colloid-containing plasma substitutes can be used in emergency treatment of shock, albumin has a prolonged intravascular half-life. When blood volume deficit is the result of hemorrhage, compatible red blood cells or whole blood should be administered as quickly as possible.

Hypoalbuminemia

Hypoalbuminemia is another possible indication for use of albumin purified and made available by the method of the current invention, 25% Solution, Buminate 25%. Hypoalbuminemia can result from one or more of the following: Inadequate production (malnutrition, burns, major injury, infections, etc.); Excessive catabolism (burns, major injury, pancreatitis, etc.); Loss from the body (hemorrhage, excessive renal excretion, burn exudates, etc.); and Redistribution within the body (major surgery, various inflammatory conditions, etc.).

When albumin deficit is the result of excessive protein loss, the effect of administration of albumin will be temporary unless the underlying disorder is reversed. In most cases, increased nutritional replacement of amino acids and/or protein with concurrent treatment of the underlying disorder will restore normal plasma albumin levels more effectively than albumin solutions. Occasionally hypoalbuminemia accompanying severe injuries, infections or pancreatitis cannot be quickly reversed and nutritional supplements may fail to restore serum albumin levels. In these cases, albumin (Human), 25% Solution, Buminate 25% might be a useful therapeutic adjunct.

Burns

An optimum regimen for the use of albumin, electrolytes and fluid in the early treatment of burns has not been established, however, in conjunction with appropriate crystalloid therapy, Albumin (Human), 25% Solution, Buminate 25% may be indicated for treatment of oncotic deficits after the initial 24 hour period following extensive burns and to replace the protein loss which accompanies any severe burn.

Adult Respiratory Distress Syndrome (ARDS)

A characteristic of ARDS is a hypoproteinemic state which may be causally related to the interstitial pulmonary edema. Although uncertainty exists concerning the precise indication of albumin infusion in these patients, if there is a pulmonary overload accompanied by hypoalbuminemia, 25% albumin solution may have a therapeutic effect when used with a diuretic.

Nephrosis

Albumin (Human), 25% Solution may be a useful aid in treating edema in patients with severe nephrosis who are receiving steroids and/or diuretics.

Cardiopulmonary Bypass Surgery

Albumin (Human), 25% Solution, Buminate 25% has been recommended prior to or during cardiopulmonary bypass surgery, although no clear data exist indicating its advantage over crystalloid solutions.

Hemolytic Disease of the Newborn (HDN)

Albumin (Human), 25% Solution, Buminate 25% may be administered in an attempt to bind and detoxify unconjugated bilirubin in infants with severe HDN.

It is also possible to use the albumin purified by means of the current invention as an excipient for the delivery of pharmaceuticals.

Crystal Screening Experiments

The hanging drop screens are made in boxes with 24 wells divided in 4 rows (A, B, C, D) and 6 columns. The screens are presented in the preliminary report only as lists of the reagents as follows. A brief comment to the results is provided. In the final report the results are provided in tables with complete details similar to the following example tables.

Microscopy and Tables

The sample evaluations by microscopy are made in the beginning of experiments with 2–3 days frequency and later on once a week. The microscopy observations in the tables are in abbreviated form using the following letters:

N=no precipitation or other phase separation

C=Some crystals present

CC=A significant amount of crystals present

A=amorphous precipitate, cloud of non-transparent particles looking like cloud or brownish smoke, size of the particles is near the lowest limit of separation power of light microscope AA=A significant amount of amorphous precipitate L=liquid phase separation, spherical transparent droplets, looking like oil in water LL=A significant liquid separation G=gel lumps, irregular glassy transparent particles of several micrometers in diameter GG=A significant amount of gel X=contaminated or dried drop, discontinued experiment

TABLE 11

Reverse temperature effect with amorphous precipitate. Precipitates increases at higher temperature under microscopy. Crystals were very temperature sensitive, they dissolve at higher temperature.

| | |
|---|---|
| Start date (d, m, y): 17.8.2001 | Microscopy observations |
| Sample: GTC hSA: labeled 7F-5AC | C = crystals |
| Drop: 8 µl sample + 2 µl reagent | A = amorphous precipitate |
| Temperatures: +25° C. or +4° C. | L = liquid phase separation, spherical droplets |
| Initial protein concentration: 11.7 mg/ml | G = gel, glassy solid irregular particles |
| Final protein concentration: 58 mg/ml | N = no phase separations, clear solution |
| Buffer: 0.05 M K—Na-phosphate pH 7.4 | X = experiment failed, discontinued, dried, microbial contamination etc. |

| well | Reagents | 3 d +25° C. | 3 d +4° C. | 8 d, +4° C. | 27 d, +4° C. |
|---|---|---|---|---|---|
| A1 | 17% PEG 3350 0.08% decanol | N | N | L, G | N |
| A2 | 18% PEG 3350 0.08% decanol | N | N | L | N |
| A3 | 19% PEG 3350 0.08% decanol | N | N | C | CC |
| A4 | 22% PEG 3350 0.08% decanol | N | N | L, G | N |
| A5 | 25% PEG 3350 0.08% decanol | N | N | G | N |
| A6 | 30% PEG 3350 0.08% decanol | AA | A, GG | G | GG |
| B1 | 17% PEG 3350 0.36% decanol | N | N | N | N |

TABLE 11-continued

Reverse temperature effect with amorphous precipitate. Precipitates increases at higher temperature under microscopy. Crystals were very temperature sensitive, they dissolve at higher temperature.

Figure 14:
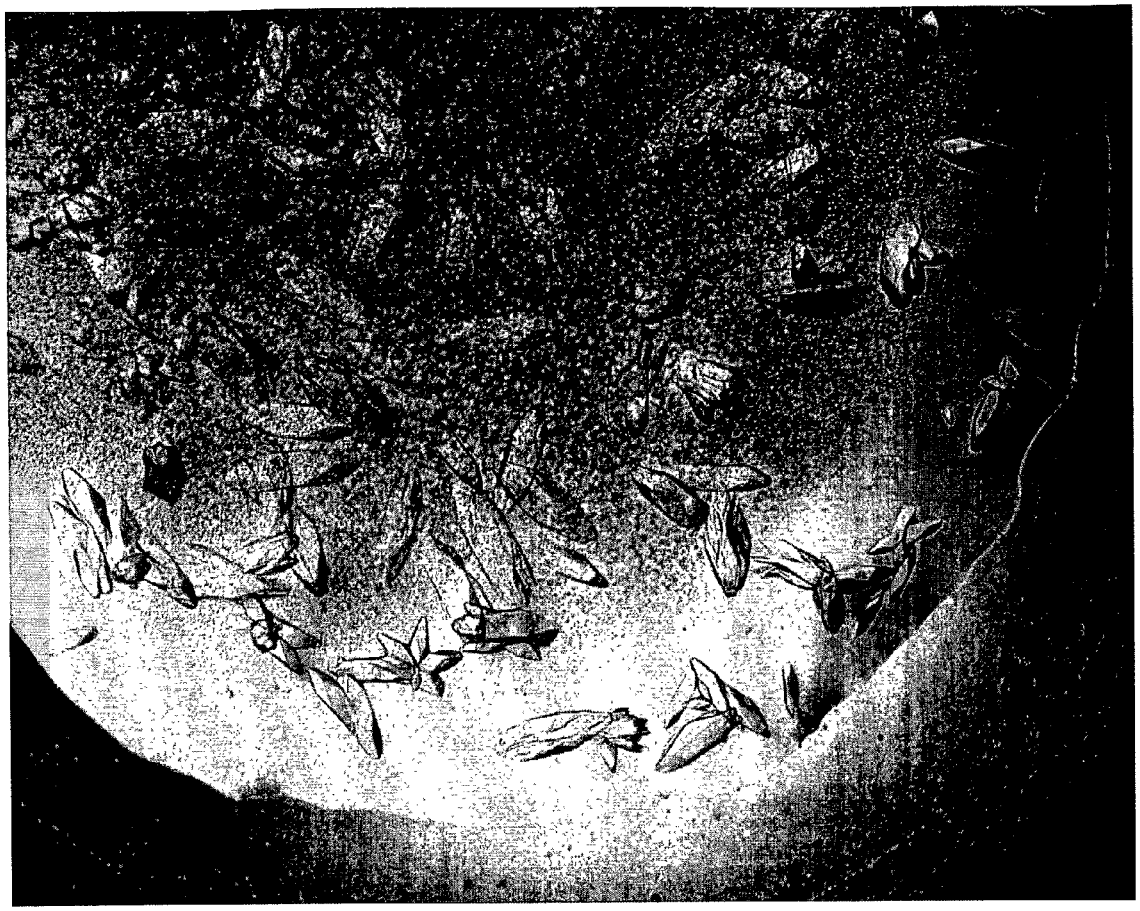
FIG. 14 shows, albumin crystals of the invention along with more amorphous precipitate. The typical crystal size is approximately 0.1×0.4 mm. The precipitate disappears over time becomes crystalline. The crystals were prepared at 4° C. in 2.7 Molar ammonium sulfate containing 0.08% decanol; 0.05 M Na—K phosphate at pH 7.4. Crystallized at 4° C.' hSA 58.7 mg/ml.

| | | | | | |
|---|---|---|---|---|---|
| B2 | 18% PEG 3350 0.36% decanol | N | N | N | N |
| B3 | 19% PEG 3350 0.36% decanol | N | N | N | N |
| B4 | 22% PEG 3350 0.36% decanol | N | N | A | N |
| B5 | 25% PEG 3350 0.36% decanol | N | L, GG | G | N |
| B6 | 30% PEG 3350 0.36% decanol | AA | A | L, G | GG, LL |
| C1 | 1.5 M (NH$_4$)$_2$SO$_4$ 0.08% decanol | N | N | N | N |
| C2 | 1.65 M (NH$_4$)$_2$SO$_4$ 0.08% decanol | N | N | N | N |
| C3 | 1.8 M (NH$_4$)$_2$SO$_4$ 0.08% decanol | N | N | N | N |
| C4 | 2.1 M (NH$_4$)$_2$SO$_4$ 0.08% decanol | N | N | N | N |
| C5 | 2.4 M (NH$_4$)$_2$SO$_4$ 0.08% decanol | G | A, GG | C, A | C, L |
| C6 | 2.7 M (NH$_4$)$_2$SO$_4$ 0.08% decanol | GG | CC, G FIG. 14 | CC, G | CC, G |
| D1 | 1.5 M (NH$_4$)$_2$SO$_4$ 0.36% decanol | N | N | N | N |
| D2 | 1.65 M (NH$_4$)$_2$SO$_4$ 0.36% decanol | N | N | N | N |
| D3 | 1.8 M (NH$_4$)$_2$SO$_4$ 0.36% decanol | N | N | N | N |
| D4 | 2.1 M (NH$_4$)$_2$SO$_4$ 0.36% decanol | N | A | N | N |
| D5 | 2.4 M (NH$_4$)$_2$SO$_4$ 0.36% decanol | AA | C, G | L | LL |
| D6 | 2.7 M (NH$_4$)$_2$SO$_4$ 0.36% decanol | L, A, GG | CC, G | C, G | CC, G |

MCS 23 AAT, Sample: GTC hSA: labeled 7F-5AC; PEG 3350 or (NH$_4$)$_2$SO$_4$ buffered with 0.05 M K—Na-phosphatepH 7.4 effect of decanol additive.
Row A: 500 μl of PEG 3350 17, 18, 19, 22, 25 or 30% in 0.05 M K—Na-phosphate pH 7.4; add 10 μl 4% decanol to each 500 μlof A reagents to get final 0.08% decanol.
Row B: like row A, but add 50 μl 4% decanol to each 500 μl of A reagents to get final 0.36% decanol.
Row C: 500 μl of (NH$_4$)$_2$SO$_4$ 1.5, 1.65, 1.8, 2.1, 2.4 or 2.7 M in 0.05 M K—Na-phosphate pH 7.4; add 10 μl4% decanol to each 500 μl of A reagents to get final 0.08% decanol.
Row D: like row C, but add 50 μl 4% decanol to each 500 μl of A reagents to get final 0.36% decanol.
Results: Crystals of high quality (FIG. 14) were produced with 2.4 M and 2.7 M ammonium sulfate-decanol combinations Crystals of adifferent habit were produced with 19% PEG, 0.08% decanol. Amorphous or gel precipitates were also produced with both reagents.Crystallization is very critically related to the reagent concentration and temperature.

TABLE 12

| | |
|---|---|
| Start date (d, m, y): 17.8.2001 | Microscopy observations |
| Sample: Sigma A-9511 | C = crystals |
| Drop: 2 μl sample + 2 μl reagent | A = amorphous precipitate |
| Temperatures: +25° C. or +7° C. | L = liquid phase separation, spherical droplets |
| Initial protein concentration: 55 mg/ml | G = gel, glassy solid irregular particles |
| Final protein concentration: 110 mg/ml | N = no phase separations, clear solution |
| Buffer: 0.05 M K—Na-phosphate pH 7 | X = experiment failed, discontinued, dried, microbial contamination etc. |

| well | Reagents | 3 d +25° C. | 3 d +7° C. | 8 d, +7° C. | 27 d, +7° C. |
|---|---|---|---|---|---|
| A1 | 17% PEG 3350 0.08% decanol | N | N | G | N |
| A2 | 18% PEG 3350 0.08% decanol | N | N | L | A |
| A3 | 19% PEG 3350 0.08% decanol | N | N | A | N |
| A4 | 22% PEG 3350 0.08% decanol | N | N | A | N |
| A5 | 25% PEG 3350 0.08% decanol | N | N | A | N |
| A6 | 30% PEG 3350 0.08% decanol | AA | AA | A | AA |
| B1 | 17% PEG 3350 0.36% decanol | N | N | N | N |
| B2 | 18% PEG 3350 0.36% decanol | N | N | N | N |
| B3 | 19% PEG 3350 0.36% decanol | N | N | N | N |
| B4 | 22% PEG 3350 0.36% decanol | N | N | A | N |
| B5 | 25% PEG 3350 0.36% decanol | N | N | N | N |
| B6 | 30% PEG 3350 0.36% decanol | N | N | L, G | GG |
| C1 | 1.5 M (NH$_4$)$_2$SO$_4$ 0.08% decanol | N | N | N | N |
| C2 | 1.65 M (NH$_4$)$_2$SO$_4$ 0.08% decanol | N | N | N | N |
| C3 | 1.8 M (NH$_4$)$_2$SO$_4$ 0.08% decanol | N | N | N | N |
| C4 | 2.1 M (NH$_4$)$_2$SO$_4$ 0.08% decanol | N | A | A | N |
| C5 | 2.4 M (NH$_4$)$_2$SO$_4$ 0.08% decanol | GG | GG | GG | LL, AA |
| C6 | 2.7 M (NH$_4$)$_2$SO$_4$ 0.08% decanol | GG | GG | GG | GG |
| D1 | 1.5 M (NH$_4$)$_2$SO$_4$ 0.36% decanol | GG | GG | C | C |
| D2 | 1.65 M (NH$_4$)$_2$SO$_4$ 0.36% decanol | N | N | N | N |
| D3 | 1.8 M (NH$_4$)$_2$SO$_4$ 0.36% decanol | N | N | N | N |
| D4 | 2.1 M (NH$_4$)$_2$SO$_4$ 0.36% decanol | N | A | N | N |
| D5 | 2.4 M (NH$_4$)$_2$SO$_4$ 0.36% decanol | N | A | L | L, A, G |
| D6 | 2.7 M (NH$_4$)$_2$SO$_4$ 0.36% decanol | LL, G | LL, GG | GG | GG |

TABLE 12-continued

Table 12 above, MCS 22 AAS, Sample: Sigma hSA, A-9511
PEG 3350 or $(NH_4)_2SO_4$ buffered with 0.05 M K—Na-phosphate pH 7.4
effect of decanol additive Similar screen to table 11.
Results: Sigma hSA did not crystallize as well as GTC hSA 7F-5AC. Only one sample in 1.5 M $(NH_4)_2SO_4$, 0.36%decanol produced high quality crystals.

TABLE 13

Reverse temperature effect with amorphous precipitate, precipitates increase at higher temperature under microscopy. Crystals were very temperature sensitive, they dissolve at higher temperature.

Box code: MCS 22AT
Start date (d, m, y): 17.8.2001
Sample: GTC hSA: labeled 7F-5AC
Drop: 8 μl sample + 2 μl reagent
Temperatures: +25° C. or +7° C.
Initial protein concentration: 11.7 mg/ml
Final protein concentration: 58 mg/ml
Buffer: 0.05 M K—Na-phosphate pH 7.4

Microscopy observations
C = crystals
A = amorphous precipitate
L = liquid phase separation, spherical droplets
G = gel, glassy solid irregular particles
N = no phase separations, clear solution
X = experiment failed, discontinued, dried, microbial contamination etc.

| well | Reagents | 1 d +25° C. | 4 d +25° C. | 30 d, +7° C. | d, ° C. |
|---|---|---|---|---|---|
| A1 | 17% PEG 3350 | N | N | N | |
| A2 | 18% PEG 3350 | N | N | N | |
| A3 | 19% PEG 3350 | N | N | N | |
| A4 | 22% PEG 3350 | N | N | A | |
| A5 | 25% PEG 3350 | N | N | N | |
| A6 | 30% PEG 3350 | LL | LL | A, G | |
| B1 | 17% PEG 3350 0.4% caprylic acid | N | N | A | |
| B2 | 18% PEG 3350 0.4% caprylic acid | N | N | A | |
| B3 | 19% PEG 3350 0.4% caprylic acid | N | N | A | |
| B4 | 22% PEG 3350 0.4% caprylic acid | N | N | N | |
| B5 | 25% PEG 3350 0.4% caprylic acid | N | N | A, L | |
| B6 | 30% PEG 3350 0.4% caprylic acid | LL | LL | A, L | |
| C1 | 1.5 M $(NH_4)_2SO_4$ | N | N | N | |
| C2 | 1.65 M $(NH_4)_2SO_4$ | N | N | N | |
| C3 | 1.8 M $(NH_4)_2SO_4$ | N | N | N | |
| C4 | 2.1 M $(NH_4)_2SO_4$ | N | N | A | |
| C5 | 2.4 M $(NH_4)_2SO_4$ | A | N | A, G | |
| C6 | 2.7 M $(NH_4)_2SO_4$ | GG | C, G | A, G | |
| D1 | 1.5 M $(NH_4)_2SO_4$ 0.4% caprylic acid | N | N | N | |
| D2 | 1.65 M $(NH_4)_2SO_4$ 0.4% caprylic acid | N | N | N | |
| D3 | 1.8 M $(NH_4)_2SO_4$ 0.4% caprylic acid | N | N | N | |
| D4 | 2.1 M $(NH_4)_2SO_4$ 0.4% caprylic acid | N | N | A | |
| D5 | 2.4 M $(NH_4)_2SO_4$ 0.4% caprylic acid | N | LL, GG | A | |
| D6 | 2.7 M $(NH_4)_2SO_4$ 0.4% caprylic acid | L, G | LL, GG | A | |

For table 13 MCS 22 AT, Sample: GTC hSA: labeled 7F-5AC
PEG 3350 or $(NH_4)_2SO_4$ buffered with 0.05 M K—Na-phosphate pH 7.4
effect of caprylic acid additive.
Results: Unstable crystals were produced in only 2.7 M $(NH_4)_2SO_4$ without caprylic acid.

TABLE 14

Start date (d, m, y): 17.8.2001
Sample: Sigma A-9511
Drop: 2 μl sample + 2 μl reagent
Temperatures: +25° C. or +7° C.
Initial protein concentration: 55 mg/ml
Final protein concentration: 110 mg/ml
Buffer: 0.05 M K—Na-phosphate pH 7.4

Microscopy observations
C = crystals
A = amorphous precipitate
L = liquid phase separation, spherical droplets
G = gel, glassy solid irregular particles
N = no phase separations, clear solution
X = experiment failed, discontinued, dried, microbial contamination etc.

| well | Reagents | 1 d +25° C. | 4 d +25° C. | 30 d, +7° C. | d, ° C. |
|---|---|---|---|---|---|
| A1 | 17% PEG 3350 | N | N | A, G | |
| A2 | 18% PEG 3350 | N | N | N | |
| A3 | 19% PEG 3350 | N | X | X | |
| A4 | 22% PEG 3350 | N | X | X | |
| A5 | 25% PEG 3350 | N | X | X | |
| A6 | 30% PEG 3350 | GG | AA | X | |
| B1 | 17% PEG 3350 0.4% caprylic acid | N | N | A, G | |
| B2 | 18% PEG 3350 0.4% caprylic acid | N | N | A, G | |

TABLE 14-continued

| | | | | |
|---|---|---|---|---|
| B3 | 19% PEG 3350 0.4% caprylic acid | N | N | A, G |
| B4 | 22% PEG 3350 0.4% caprylic acid | N | N | N |
| B5 | 25% PEG 3350 0.4% caprylic acid | N | N | N |
| B6 | 30% PEG 3350 0.4% caprylic acid | A | A | N |
| C1 | 1.5 M $(NH_4)_2SO_4$ | N | N | N |
| C2 | 1.65 M $(NH_4)_2SO_4$ | N | N | N |
| C3 | 1.8 M $(NH_4)_2SO_4$ | N | N | N |
| C4 | 2.1 M $(NH_4)_2SO_4$ | A | N | A |
| C5 | 2.4 M $(NH_4)_2SO_4$ | GG | GG | AA |
| C6 | 2.7 M $(NH_4)_2SO_4$ | GG | GG | AA |
| D1 | 1.5 M $(NH_4)_2SO_4$ 0.4% caprylic acid | N | N | N |
| D2 | 1.65 M $(NH_4)_2SO_4$ 0.4% caprylic acid | N | N | N |
| D3 | 1.8 M $(NH_4)_2SO_4$ 0.4% caprylic acid | N | N | N |
| D4 | 2.1 M $(NH_4)_2SO_4$ 0.4% caprylic acid | A, G | A, G | A, G |
| D5 | 2.4 M $(NH_4)_2SO_4$ 0.4% caprylic acid | A, G | GG | AA |
| D6 | 2.7 M $(NH_4)_2SO_4$ 0.4% caprylic acid | GG | GG | AA |

MCS 22 AT, Sample: Sigma hSA, A-9511
PEG 3350 or $(NH_4)_2SO_4$ buffered with 0.05 M K—Na-phosphate pH 7.4
effect of caprylic acid additive. Similar screen to the table 3.
Results: No crystals produced. Only precipitates at the higher reagent concentrations.

TABLE 15

Start date (d, m, y): 10.8.2001
Sample: GTC hSA: labeled 7F-5AC
Drop: 5 µl sample + 1 µl reagent
Temperatures +7° C.
Initial protein concentration: 12.2 mg/ml
Final protein concentration: 73 mg/ml
Buffers: 0.1 M Na—K-phosphates pH 5.0–7.0

Microscopy observations
C = crystals
A = amorphous precipitate
L = liquid phase separation, spherical droplets
G = gel, glassy solid irregular particles
N = no phase separations, clear solution
X = experiment failed, discontinued, dried, microbial contamination etc.

| | | number of days (d), temperature (° C.) | | | |
|---|---|---|---|---|---|
| well | Reagents | 3 d, +7° C. | 8 d, +7° C. | 10 d, +7° C. | 40 d, +7° C. |
| A1 | 1.0 M $(NH_4)_2SO_4$ pH5.0 | N | A | A, G | A, G |
| A2 | 1.0 M $(NH_4)_2SO_4$ pH 5.6 | N | N | N | N |
| A3 | 1.0 M $(NH_4)_2SO_4$ pH 5.9 | N | N | N | N |
| A4 | 1.0 M $(NH_4)_2SO_4$ pH 6.2 | N | N | N | N |
| A5 | 1.0 M $(NH_4)_2SO_4$ pH 6.6 | N | N | N | N |
| A6 | 1.0 M $(NH_4)_2SO_4$ pH 7.0 | N | N | N | N |
| B1 | 1.5 M $(NH_4)_2SO_4$ pH 5.0 | N | AA, GG | G | A, G |
| B2 | 1.5 M $(NH_4)_2SO_4$ pH 5.6 | N | N | A | A |
| B3 | 1.5 M $(NH_4)_2SO_4$ pH 5.9 | N | N | A | A |
| B4 | 1.5 M $(NH_4)_2SO_4$ pH 6.2 | N | N | A | A |
| B5 | 1.5 M $(NH_4)_2SO_4$ pH 6.6 | N | N | A | A |
| B6 | 1.5 M $(NH_4)_2SO_4$ pH 7.0 | N | N | A | A |
| C1 | 2.0 M $(NH_4)_2SO_4$ pH 5.0 | AA | AA | GG | A, G |
| C2 | 2.0 M $(NH_4)_2SO_4$ pH 5.6 | N | AA, G | GG | A |
| C3 | 2.0 M $(NH_4)_2SO_4$ pH 5.9 | N | AA, C | GG | A |
| C4 | 2.0 M $(NH_4)_2SO_4$ pH 6.2 | AA, C | AA | GG, C | A |
| C5 | 2.0 M $(NH_4)_2SO_4$ pH 6.6 | A | A | CC | A |
| C6 | 2.0 M $(NH_4)_2SO_4$ pH 7.0 | A | A | CC | A |
| D1 | 3.0 M $(NH_4)_2SO_4$ pH 5.0 | AA, L | AA, GG | GG | A, G |
| D2 | 3.0 M $(NH_4)_2SO_4$ pH 5.6 | AA, L | AA, GG | GG | A |
| D3 | 3.0 M $(NH_4)_2SO_4$ pH 5.9 | AA, L | AA, GG | GG | A, G |
| D4 | 3.0 M $(NH_4)_2SO_4$ pH 6.2 | A | AA, GG | GG | A |
| D5 | 3.0 M $(NH_4)_2SO_4$ pH 6.6 | A | AA, GG | GG | A, G |
| D6 | 3.0 M $(NH_4)_2SO_4$ pH 7.0 | AA, L | AA, GG | GG | A, G |

MCS16 Sample: GTC hSA: labeled 7F-5AC
Ammonium sulfate buffered with phosphates
4 rows: A 1, 0 M, B 1, 5 M, C 2, 0 M, D 3, 0 M
6 columns: 0, 1 M phosphates pH 5.0 pH 5.6 pH 5.9 pH 6.2 pH 6.6 pH 7.0
Results: Amorphous precipitates above 2 M. So Me unstable poor quality crystals which disappeared in 40 d storage.

TABLE 16

Start date (d, m, y): 10.8.2001
Sample: GTC hSA: labeled 7F-5AC
Drop: 5 µl sample + 1 µl reagent
Temperatures +7° C.

Microscopy observations
C = crystals
A = amorphous precipitate
L = liquid phase separation, spherical droplets

TABLE 16-continued

| Initial protein concentration: 12.2 mg/ml | G = gel, glassy solid irregular particles |
| Final protein concentration: 73 mg/ml | N = no phase separations, clear solution |
| Buffers: 0.1 M Na—K-phosphates pH 5.0–7.0 | X = experiment failed, discontinued, dried, microbial contamination etc. |

| | | number of days (d), temperature (° C.) | | | |
|---|---|---|---|---|---|
| well | Reagents | 3 d, +7° C. | 6 d, +7° C. | 10 d, +7° C. | 40 d, +7° C. |
| A1 | 1.0 M sodium sulfate pH 5.0 | N | N | N | N |
| A2 | 1.0 M sodium sulfate pH 5.6 | N | N | N | N |
| A3 | 1.0 M sodium sulfate pH 5.9 | N | N | N | N |
| A4 | 1.0 M sodium sulfate pH 6.2 | N | N | N | N |
| A5 | 1.0 M sodium sulfate pH 6.6 | N | N | N | N |
| A6 | 1.0 M sodium sulfate pH 7.0 | N | N | N | N |
| B1 | 1.5 M sodium sulfate pH 5.0 | N | N | AA | A |
| B2 | 1.5 M sodium sulfate pH 5.6 | N | N | AA | A |
| B3 | 1.5 M sodium sulfate pH 5.9 | N | N | AA | A |
| B4 | 1.5 M sodium sulfate pH 6.2 | N | N | AA | A |
| B5 | 1.5 M sodium sulfate pH 6.6 | N | N | AA | A |
| B6 | 1.5 M sodium sulfate pH 7.0 | N | N | AA | A |
| C1 | 1.75 M sodium sulfate pH 5.0 | N | G, C | AA | A |
| C2 | 1.75 M sodium sulfate pH 5.6 | N | A, G | AA | A |
| C3 | 1.75 M sodium sulfate pH 5.9 | N | A | AA | A |
| C4 | 1.75 M sodium sulfate pH 6.2 | N | N | AA | A |
| C5 | 1.75 M sodium sulfate pH 6.6 | N | N | AA | A |
| C6 | 1.75 M sodium sulfate pH 7.0 | N | N | AA | A |
| D1 | 2.0 M sodium sulfate pH 5.0 | AA, L | GG, C | LL, GG | A |
| D2 | 2.0 M sodium sulfate pH 5.6 | AA, L | GG | LL, GG | A |
| D3 | 2.0 M sodium sulfate pH 5.9 | AA, L | GG, C | A, GG | A |
| D4 | 2.0 M sodium sulfate pH 6.2 | AA, LL | GG, L, C | L, GG | G, A |
| D5 | 2.0 M sodium sulfate pH 6.6 | AA, LL | G, L, C | L, GG | G, A |
| D6 | 2.0 M sodium sulfate pH 7.0 | A, LL | GG | AA | G, A |

Crystals were not stable.
MCS17, Sample: GTC hSA: labeled 7F-5AC
Sodium sulfate buffered with phosphates
4 rows: A 1, 0 M, B 1, 5 M, C 1.75 M, D 2.0 M Na$_2$SO$_4$
6 columns: 0, 1 M phosphates pH 5.0 pH 5.6 pH 5.9 pH 6.2 pH 6.6 pH 7.0
Results: Unstable crystals in 1.75 M and 2.0 M Na$_2$SO$_4$
Precipitation, amorphous and gel in 1.5–2.0 M Na$_2$SO$_4$

TABLE 17

| Start date (d, m, y): 28.8.2001 | Microscopy observations |
| Sample: GTC hSA: labeled 7F-5AC | C = crystals |
| Drop: 5 μl sample + 2 μl reagent | A = amorphous precipitate |
| Temperatures +7° C. | L = liquid phase separation, spherical droplets |
| Initial protein concentration: 10.3 mg/ml | G = gel, glassy solid irregular particles |
| Final protein concentration: 36 mg/ml | N = no phase separations, clear solution |
| Buffers: 0.1 M Na—K-phosphates pH 6.6–7.8 | X = experiment failed, discontinued, dried, microbial contamination etc. |

| | | number of days (d), temperature (° C.) | | |
|---|---|---|---|---|
| well | Reagents: 0.36% decanol in all samples | 12 d, +7° C. | 22 d, +7° C. | 28 d, +7° C. |
| A1 | 1.6 M Na—K-phosphate pH 6.6 | L | N | N |
| A2 | 1.6 M Na—K-phosphate pH 7.0 | L | N | N |
| A3 | 1.6 M Na—K-phosphate pH 7.2 | L | N | N |
| A4 | 1.6 M Na—K-phosphate pH 7.4 | L | N | N |
| A5 | 1.6 M Na—K-phosphate pH 7.6 | L | N | N |
| A6 | 1.6 M Na—K-phosphate pH 7.8 | G | N | N |
| B1 | 1.8 M Na—K-phosphate pH 6.6 | L | N | N |
| B2 | 1.8 M Na—K-phosphate pH 7.0 | L | N | N |
| B3 | 1.8 M Na—K-phosphate pH 7.2 | N | N | N |
| B4 | 1.8 M Na—K-phosphate pH 7.4 | N | N | N |
| B5 | 1.8 M Na—K-phosphate pH 7.6 | N | N | N |
| B6 | 1.8 M Na—K-phosphate pH 7.8 | L, G | N | N |
| C1 | 2.0 M Na—K-phosphate pH 6.6 | L | N | N |
| C2 | 2.0 M Na—K-phosphate pH 7.0 | L | N | N |
| C3 | 2.0 M Na—K-phosphate pH 7.2 | L | N | N |
| C4 | 2.0 M Na—K-phosphate pH 7.4 | L | N | N |
| C5 | 2.0 M Na—K-phosphate pH 7.6 | L | N | N |
| C6 | 2.0 M Na—K-phosphate pH 7.8 | L, G | N | N |

TABLE 17-continued

| | | | | |
|---|---|---|---|---|
| D1 | 2.2 M Na—K-phosphate pH 6.6 | L | N | L |
| D2 | 2.2 M Na—K-phosphate pH 7.0 | CC | N | L |
| D3 | 2.2 M Na—K-phosphate pH 7.2 | CC | N | L |
| D4 | 2.2 M Na—K-phosphate pH 7.4 | CC | N | L |
| D5 | 2.2 M Na—K-phosphate pH 7.6 | CC | N | CC, L |
| D6 | 2.2 M Na—K-phosphate pH 7.8 | CC | N | CC, L |

Note: Crystals were not stable when moved to room temperature for microscopy.
MCSA30, Sample: GTC hSA: labeled 7F-5AC
1.6–2.2 M K—Na-phosphates pH 6.6–7.8, 0.36% decanol in all drops
Results: Good quality crystals in 2.2 M phosphates pH 7.0–7.8. The crystals were very temperature sensitive, they dissolved afterMicroscopy at room temperature and crystallized again in refrigerator.

TABLE 18

| | | number of days (d), temperature (° C.) | | | |
|---|---|---|---|---|---|
| well | Reagents | 3 d, +7° C. | 8 d, +7° C. | 10 d, +7° C. | 40 d, +7° C. |
| A1 | 1.2 M Na—K-phosphate pH 4.3 | N | N | N | G, A |
| A2 | 1.2 M Na—K-phosphate pH 5.0 | N | N | N | N |
| A3 | 1.2 M Na—K-phosphate pH 5.3 | N | N | N | N |
| A4 | 1.2 M Na—K-phosphate pH 5.6 | N | N | N | N |
| A5 | 1.2 M Na—K-phosphate pH 5.9 | N | N | N | N |
| A6 | 1.2 M Na—K-phosphate pH 6.2 | N | N | N | N |
| B1 | 1.6 M Na—K-phosphate pH 4.3 | N | A | A | G, A |
| B2 | 1.6 M Na—K-phosphate pH 5.0 | N | N | A | G, A |
| B3 | 1.6 M Na—K-phosphate pH 5.3 | N | N | A | A |
| B4 | 1.6 M Na—K-phosphate pH 5.6 | N | N | N | N |
| B5 | 1.6 M Na—K-phosphate pH 5.9 | N | N | N | A |
| B6 | 1.6 M Na—K-phosphate pH 6.2 | N | N | N | A |
| C1 | 1.8 M Na—K-phosphate pH 4.3 | N | AA, GG | A | A, G |
| C2 | 1.8 M Na—K-phosphate pH 5.0 | N | AA | A | A, G |
| C3 | 1.8 M Na—K-phosphate pH 5.3 | N | N | A | A |
| C4 | 1.8 M Na—K-phosphate pH 5.6 | N | N | A | A |
| C5 | 1.8 M Na—K-phosphate pH 5.9 | N | N | A | A |
| C6 | 1.8 M Na—K-phosphate pH 6.2 | N | N | A | A |
| D1 | 2.2 M Na—K-phosphate pH 4.3 | AA | AA, GG | GG | A, G |
| D2 | 2.2 M Na—K-phosphate pH 5.0 | N | AA | AA | A, G |
| D3 | 2.2 M Na—K-phosphate pH 5.3 | N | GG, C | G | A, G |
| D4 | 2.2 M Na—K-phosphate pH 5.6 | N | N | A | A |
| D5 | 2.2 M Na—K-phosphate pH 5.9 | N | N | A | A |
| D6 | 2.2 M Na—K-phosphate pH 6.2 | N | N | A, G | A, G |

Notes:
Reverse temperature effect; amorphous precipitate increases at higher temperature under microscopy. Crystals were not stable, they dissolved at higher temperature under microscopy.
Start date (d, m, y): 10.8.2001
Sample: GTC hSA: labeled 7F-5AC
Drop: 5 μl sample + 1 μl reagent
temperatures +7° C.
Initial protein concentration: 12.2 mg/ml
Final protein concentration: 73 mg/ml
Buffers: Na—K-phosphates pH 4.3–6.2 pH
Microscopy observations
C = crystals
A = amorphous precipitate
L = liquid phase separation, spherical droplets
G = gel, glassy solid irregular particles
N = no phase separations, clear solution
X = experiment failed, discontinued, dried, microbial contamination etc.

TABLE 19

| | | number of days (d), temperature (° C.) | | | |
|---|---|---|---|---|---|
| well | Reagents | 3 d, +7° C. | 8 d, +7° C. | 10 d, +7° C. | 40 d, +7° C. |
| A1 | 1.2 M Na—K-phosphate pH 6.6 | N | N | N | N |
| A2 | 1.2 M Na—K-phosphate pH 7.0 | N | N | N | N |
| A3 | 1.2 M Na—K-phosphate pH 7.4 | N | N | N | N |
| A4 | 1.2 M Na—K-phosphate pH 7.7 | N | N | N | N |
| A5 | 1.2 M Na—K-phosphate pH 8.2 | N | N | N | N |
| A6 | | | | | |
| B1 | 1.6 M Na—K-phosphate pH 6.6 | N | N | A | A |

TABLE 19-continued

| | | number of days (d), temperature (° C.) | | | |
|---|---|---|---|---|---|
| well | Reagents | 3 d, +7° C. | 8 d, +7° C. | 10 d, +7° C. | 40 d, +7° C. |
| B2 | 1.6 M Na—K-phosphate pH 7.0 | N | N | A | A |
| B3 | 1.6 M Na—K-phosphate pH 7.4 | A | AA, GG | A | A |
| B4 | 1.6 M Na—K-phosphate pH 7.7 | N | N | N | N |
| B5 | 1.6 M Na—K-phosphate pH 8.2 | N | N | N | N |
| B6 | | | | | |
| C1 | 1.8 M Na—K-phosphate pH 6.6 | N | N | A | A |
| C2 | 1.8 M Na—K-phosphate pH 7.0 | N | N | A | A |
| C3 | 1.8 M Na—K-phosphate pH 7.4 | AA | AA, GG | CC, GG | AA |
| C4 | 1.8 M Na—K-phosphate pH 7.7 | N | AA | GG | A |
| C5 | 1.8 M Na—K-phosphate pH 8.2 | N | AA | GG | A |
| C6 | | | | | |
| D1 | 2.2 M Na—K-phosphate pH 6.6 | A | CC, A | GG | G, A |
| D2 | 2.2 M Na—K-phosphate pH 7.0 | A | CC, G | GG | G, A |
| D3 | 2.2 M Na—K-phosphate pH 7.4 | AA, L | GG, LL | GG | G, A |
| D4 | 2.2 M Na—K-phosphate pH 7.7 | AA | AA | GG | AA |
| D5 | 2.2 M Na—K-phosphate pH 8.2 | AA | AA | GG | AA |
| D6 | | | | | |

Tables 18 and 19
MCS 15/1 and MCS 15/2, Sample: GTC hSA: labeled 7F-5AC
Phosphates without any other additives
pH 4,3–8,2 Na—K-PO$_4$ concentration 1,2 M–2,2 M
4 rows: A 1,2 M, B 1,6 M, C 1,8 M, D 2,2 M
11 columns: pH 4.3(NaH$_2$PO$_4$) containing: pH 5.0 pH 5.3 pH 5.6 pH 5.9 pH 6.2 pH 6.6 pH 7.0 pH 7.4 pH 7.7 pH 8.2.
Note:
reverse temperature effect; amorphous precipitates increase at higher temperature under microscopy.
Crystals were not stable, they dissolved at higher temperature under microscopy.
Start date (d, m, y): 10.8.2001
Sample: GTC hSA: labeled 7F-5AC
Drop: 5 μl sample + 1 μl reagent
Temperatures +7° C.
Initial protein concentration: 12.2 mg/ml
Final protein concentration: 73 mg/ml
Buffers: Na—K-phosphates pH 6.6–8.2
Microscopy observations
C = crystals
A = amorphous precipitate
L = liquid phase separation, spherical droplets
G = gel, glassy solid irregular particles
N = no phase separations, clear solution
X = experiment failed, discontinued, dried, microbial contamination etc.
Results: Sharp optimum for precipitate at pH 7.4. Unstable crystals above pH 6.6 and at pH 5.3.
Much potential for further study.

TABLE 20

| | | number of days (d), temperature (° C.) | |
|---|---|---|---|
| well | Reagents | 6 d, +25° C. | 30 d, +7° C. |
| A1 | 25% 2-propanol, 20 mM MgCl$_2$ | N | N |
| A2 | 30% 2-propanol, 20 mM MgCl$_2$ | G | G, A |
| A3 | 35% 2-propanol, 20 mM MgCl$_2$ | G | L, A |
| A4 | 1.5% benzyl alcohol, 20 mM MgCl$_2$ | N | A |
| A5 | 1.5% benzyl alcohol, 50 mM MgCl$_2$ | N | N |
| A6 | 1.5% benzyl alcohol, 100 mM MgCl$_2$ | N | N |
| B1 | 25% 2-propanol, 100 mM MgCl$_2$ | N | N |
| B2 | 30% 2-propanol, 100 mM MgCl$_2$ | G | G, A |
| B3 | 35% 2-propanol, 100 mM MgCl$_2$ | L | L, A |
| B4 | 1.5% benzyl alcohol, 200 mM MgCl$_2$ | N | N |
| B5 | 1.5% benzyl alcohol, 300 mM MgCl$_2$ | N | N |
| B6 | 1.5% benzyl alcohol, 400 mM MgCl$_2$ | N | N |
| C1 | 25% 2-propanol, 200 mM MgCl$_2$ | N | N |
| C2 | 30% 2-propanol, 200 mM MgCl$_2$ | G | G, A |
| C3 | 35% 2-propanol, 200 mM MgCl$_2$ | G | G, A |
| C4 | 1.25% benzyl alcohol, 20 mM MgCl$_2$ | N | N |
| C5 | 1.25% benzyl alcohol, 100 mM MgCl$_2$ | N | N |
| C6 | 1.25% benzyl alcohol, 300 mM MgCl$_2$ | N | N |
| D1 | 25% 2-propanol, 300 mM MgCl$_2$ | N | N |
| D2 | 30% 2-propanol, 300 mM MgCl$_2$ | N | N |
| D3 | 35% 2-propanol, 300 mM MgCl$_2$ | N | N |
| D4 | 1.0% benzyl alcohol, 20 mM MgCl$_2$ | N | N |
| D5 | 1.0% benzyl alcohol, 100 mM MgCl$_2$ | N | N |
| D6 | 1.0% benzyl alcohol, 300 mM MgCl$_2$ | N | N |

MCS21, Sample: GTC hSA: labeled 7F-5AC
Reagent combinations with magnesium chloride and containing 2-propanol or benzyl alcohol
Results: Only precipitates with 2-propanol conatining samples. No effects with benzyl alcohol.
Start date (d, m, y): 14.8.2001
Sample: GTC hSA: labeled 7F-5AC
Drop: 5 μl sample + 1 μl reagent
Temperatures +25° C. or 7° C.
Initial protein concentration: 12.2 mg/ml
Final protein concentration: 73 mg/ml
Buffers: 0.03 M Na-HEPES pH 7.5–7.8
Microscopy observations
C = crystals TABLE 20-continued

|  |  | number of days (d), temperature (° C.) | |
|---|---|---|---|
| well | Reagents | 6 d, +25° C. | 30 d, +7° C. |

A = amorphous precipitate
L = liquid phase separation, spherical droplets
G = gel, glassy solid irregular particles
N = no phase separations, clear solution
X = experiment failed, discontinued, dried, microbial contamination etc.

TABLE 21

|  |  | number of days (d), temperature (° C.) | | | |
|---|---|---|---|---|---|
| well | Reagents | 3 d, +7° C. | 4 d, +7° C. | 10 d, +7° C. | 40 d, +7° C. |
| A1 | 1.5 M NaCl pH 5.0 | N | N | N | N |
| A2 | 1.5 M NaCl pH 5.6 | N | N | N | N |
| A3 | 1.5 M NaCl pH 5.9 | N | N | N | N |
| A4 | 1.5 M NaCl pH 6.2 | N | N | N | N |
| A5 | 1.5 M NaCl pH 6.6 | N | N | N | N |
| A6 | 1.5 M NaCl pH 7.0 | N | N | N | N |
| B1 | 2.0 M NaCl pH 5.0 | N | N | N | N |
| B2 | 2.0 M NaCl pH 5.6 | N | N | N | N |
| B3 | 2.0 M NaCl pH 5.9 | N | N | N | N |
| B4 | 2.0 M NaCl pH 6.2 | N | N | N | N |
| B5 | 2.0 M NaCl pH 6.6 | N | N | N | N |
| B6 | 2.0 M NaCl pH 7.0 | N | N | N | N |
| C1 | 3.0 M NaCl pH 5.0 | N | N | N | N |
| C2 | 3.0 M NaCl pH 5.6 | N | N | N | N |
| C3 | 3.0 M NaCl pH 5.9 | N | N | N | N |
| C4 | 3.0 M NaCl pH 6.2 | N | N | N | N |
| C5 | 3.0 M NaCl pH 6.6 | N | N | N | N |
| C6 | 3.0 M NaCl pH 7.0 | N | N | N | N |
| D1 | 4.0 M NaCl pH 5.0 | N | N | N | N |
| D2 | 4.0 M NaCl pH 5.6 | N | N | N | N |
| D3 | 4.0 M NaCl pH 5.9 | N | N | N | N |
| D4 | 4.0 M NaCl pH 6.2 | N | N | N | N |
| D5 | 4.0 M NaCl pH 6.6 | N | N | N | N |
| D6 | 4.0 M NaCl pH 7.0 | N | N | N | N |

Sample: GTC hSA: labeled 7F-5AC
Sodium chloride buffered with phosphates
4 rows: A 1,5 M, B 2.0 M, C 3.0 M, D 4,0 M
6 columns: 0,1 M phosphates pH 5.0 pH 5.6 pH 5.9 pH 6.2 pH 6.6 pH 7.0
Results: No precipitates or phase separations
Start date (d, m, y): 10.8.2001
Sample: GTC hSA: labeled 7F-5AC
Drop: 5 μl sample + 1 μl reagent
temperatures +7° C.
Initial protein concentration: 12.2 mg/ml
Final protein concentration: 73 mg/ml
Buffers: 0.1 M Na—K-phosphates pH 5.0–7.0
Microscopy observations
C = crystals
A = amorphous precipitate
L = liquid phase separation, spherical droplets
G = gel, glassy solid irregular particles
N = no phase separations, clear solution
X = experiment failed, discontinued, dried, microbial contamination etc.

TABLE 22

|  |  | number of days (d), temperature (° C.) | | | |
|---|---|---|---|---|---|
| well | Reagents | 3 d, +7° C. | 4 d, +7° C. | 10 d, +7° C. | 40 d, +7° C. |
| A1 | 1.5 M KCl pH 5.0 | N | N | N | N |
| A2 | 1.5 M KCl pH 5.6 | N | N | N | N |
| A3 | 1.5 M KCl pH 5.9 | N | N | N | N |
| A4 | 1.5 M KCl pH 6.2 | N | N | N | N |

TABLE 22-continued

| well | Reagents | 3 d, +7° C. | 4 d, +7° C. | 10 d, +7° C. | 40 d, +7° C. |
|---|---|---|---|---|---|
| A5 | 1.5 M KCl pH 6.6 | N | N | N | N |
| A6 | 1.5 M KCl pH 7.0 | N | N | N | N |
| B1 | 2.0 M KCl pH 5.0 | N | N | N | N |
| B2 | 2.0 M KCl pH 5.6 | N | N | N | N |
| B3 | 2.0 M KCl pH 5.9 | N | N | N | N |
| B4 | 2.0 M KCl pH 6.2 | N | N | N | N |
| B5 | 2.0 M KCl pH 6.6 | N | N | N | N |
| B6 | 2.0 M KCl pH 7.0 | N | N | N | N |
| C1 | 3.0 M KCl pH 5.0 | N | N | N | N |
| C2 | 3.0 M KCl pH 5.6 | N | N | N | N |
| C3 | 3.0 M KCl pH 5.9 | N | N | N | N |
| C4 | 3.0 M KCl pH 6.2 | N | N | N | N |
| C5 | 3.0 M KCl pH 6.6 | N | N | N | N |
| C6 | 3.0 M KCl pH 7.0 | N | N | N | N |
| D1 | 3.9 M KCl pH 5.0 | N | N | N | N |
| D2 | 3.9 M KCl pH 5.6 | N | N | N | N |
| D3 | 3.9 M KCl pH 5.9 | N | N | N | N |
| D4 | 3.9 M KCl pH 6.2 | N | N | N | G, A |
| D5 | 3.9 M KCl pH 6.6 | N | N | N | G, A |
| D6 | 3.9 M KCl pH 7.0 | N | N | N | N |

Sample: GTC hSA: labeled 7F-5AC
Potassium chloride buffered with phosphates
4 rows: A 1,5 M, B 2.0 M, C 3.0 M, D 4,0 M
6 columns: 0,1 M phosphates pH 5.0 pH 5.6 pH 5.9 pH 6.2 pH 6.6 pH 7.0
Results: Mostly no precipitates or phase separations. Gel precipitates after 40 d in 3.9 M KCl pH 6.2–6.6.
Start date (d, m, y): 10.8.2001
Sample: GTC hSA: labeled 7F-5AC
Drop: 5 µl sample + 1 µl reagent
Temperature: +7° C.
Initial protein concentration: 12.2 mg/ml
Final protein concentration: 73 mg/ml
Buffers: 0.1 M Na—K-phosphates pH 5.0–7.0
Microscopy observations
C = crystals
A = amorphous precipitate
L = liquid phase separation, spherical droplets
G = gel, glassy solid irregular particles
N = no phase separations, clear solution
X = experiment failed, discontinued, dried, microbial contamination etc.

TABLE 23

Start date (d, m, y): 15.8.2001
Sample: GTC hSA: labeled 7F-5AC
Drop.: 5 µl sample + 1 µl reagent
temperatures +25° C. or +4° C.
Initial protein concentration: 12.2 mg/ml
Final protein concentration: 73 mg/ml
Buffers: 0.035 M TrisHCl pH 8.0 or 8.4

Microscopy observations
C = crystals
A = amorphous precipitate
L = liquid phase separation, spherical droplets
G = gel, glassy solid irregular particles
N = no phase separations, clear solution
X = experiment failed, discontinued, dried, microbial contamination etc.
date or number of days (temperature)

| well | Reagents | 5d, +25° C. | 30d, +4° C. |
|---|---|---|---|
| A1 | 10% PEG 6000 50 mM NH$_4$-acetate pH 8.0 | N | N |
| A2 | 10% PEG 6000 100 mM NH$_4$-acetate pH 8.0 | N | N |
| A3 | 10% PEG 6000 300 mM NH$_4$-acetate pH 8.0 | N | N |
| A4 | 10% PEG 6000 50 mM NH$_4$-acetate pH 8.4 | A, G | N |
| A5 | 10% PEG 6000 100 mM NH$_4$-acetate pH 8.4 | A, G | A |
| A6 | 10% PEG 6000 300 mM NH$_4$-acetate pH 8.4 | N | N |
| B1 | 15% PEG 6000 50 mM NH$_4$-acetate pH 8.0 | N | N |
| B2 | 15% PEG 6000 100 mM NH$_4$-acetate pH 8.0 | A | N |
| B3 | 15% PEG 6000 300 mM NH$_4$-acetate pH 8.0 | LL | L, A |
| B4 | 15% PEG 6000 50 mM NH$_4$-acetate pH 8.4 | A, G | N |
| B5 | 15% PEG 6000 100 mM NH$_4$-acetate pH 8.4 | A, G | A |
| B6 | 15% PEG 6000 300 mM NH$_4$-acetate pH 8.4 | N | N |
| C1 | 20% PEG 6000 50 mM NH$_4$-acetate pH 8.0 | A, L | X |
| C2 | 20% PEG 6000 100 mM NH$_4$-acetate pH 8.0 | N | A |
| C3 | 20% PEG 6000 300 mM NH$_4$-acetate pH 8.0 | L | L, A |
| C4 | 20% PEG 6000 50 mM NH$_4$-acetate pH 8.4 | L | A, G |

TABLE 23-continued

Start date (d, m, y): 15.8.2001
Sample: GTC hSA: labeled 7F-5AC
Drop.: 5 μl sample + 1 μl reagent
temperatures +25° C. or +4° C.
Initial protein concentration: 12.2 mg/ml
Final protein concentration: 73 mg/ml
Buffers: 0.035 M TrisHCl pH 8.0 or 8.4

Microscopy observations
C = crystals
A = amorphous precipitate
L = liquid phase separation, spherical droplets
G = gel, glassy solid irregular particles
N = no phase separations, clear solution
X = experiment failed, discontinued, dried, microbial contamination etc.
date or number of days (temperature)

| well | Reagents | 5d, +25° C. | 30d, +4° C. |
|---|---|---|---|
| C5 | 20% PEG 6000 100 mM NH$_4$-acetate pH 8.4 | G | A, G |
| C6 | 20% PEG 6000 300 mM NH$_4$-acetate pH 8.4 | L | L |
| D1 | 25% PEG 6000 50 mM NH$_4$-acetate pH 8.0 | LL | L, G |
| D2 | 25% PEG 6000 100 mM NH$_4$-acetate pH 8.0 | LL | L, G |
| D3 | 25% PEG 6000 300 mM NH$_4$-acetate pH 8.0 | LL | L, G |
| D4 | 25% PEG 6000 50 mM NH$_4$-acetate pH 8.4 | LL | A, G |
| D5 | 25% PEG 6000 100 mM NH$_4$-acetate pH 8.4 | LL | L, G, A |
| D6 | 25% PEG 6000 300 mM NH$_4$-acetate pH 8.4 | L | L, G |

Sample: GTC hSA: labeled 7F-5AC
10–25% PEG 6000, 0.05–0.3 M ammonium acetate, 0.035 M Tris-HCl pH 8.0–8.4,
Results: No crystals. Various precipitates in most of the samples.

TABLE 24

| well | Reagents | 4 d, +25° C. | 10 d, +4° C. | 30 d, +4° C. | d, ° C. |
|---|---|---|---|---|---|
| A1 | 10% PEG 400 | N | N | A | |
| A2 | 10% PEG 600 | N | N | N | |
| A3 | 10% PEG 1000 | N | N | N | |
| A4 | 10% PEG 4000 | N | N | N | |
| A5 | 10% PEG 6000 | N | N | A | |
| A6 | 10% PEG 20,000 | N | N | N | |
| B1 | 20% PEG 400 | G | A | A | |
| B2 | 20% PEG 600 | N | N | N | |
| B3 | 20% PEG 1000 | N | N | N | |
| B4 | 20% PEG 4000 | N | N | N | |
| B5 | 20% PEG 6000 | N | N | N | |
| B6 | 20% PEG 20 000 | N | N | A | |
| C1 | 30% PEG 400 | N | A | N | |
| C2 | 30% PEG 600 | N | N | L | |
| C3 | 30% PEG 1000 | N | A | N | |
| C4 | 30% PEG 4000 | A, G, L | N | N | |
| C5 | 30% PEG 6000 | N | N | N | |
| C6 | 30% PEG 20 000 | N | N | A | |
| D1 | 40% PEG 400 | N | N | N | |
| D2 | 40% PEG 600 | L | L | L | |
| D3 | 40% PEG 1000 | N | N | N | |
| D4 | 40% PEG 4000 | N | N | N | |
| D5 | 40% PEG 6000 | L | N | N | |
| D6 | 40% PEG 20 000 | LL | A, G | A, G | |

Sample: GTC hSA: labeled 7F-5AC
PEG of various molecular weights 400–20 000, phosphate buffer pH 7.4 in the sample.
Results: No crystals and mostly no precipitates, amorphous forms at the highest concentration of PEG 6000.
Start date (d, m, y): 14.8.2001
Sample: GTC hSA: labeled 7F-5AC
Drop: 5 μl sample + 1 μl reagent
temperatures: +25° C. or +4° C.
Initial protein concentration: 12.2 mg/ml
Final protein concentration: 73 mg/ml
Buffer: 0.1 M phosphate pH 7.4
Microscopy observations
C = crystals
A = amorphous precipitate
L = liquid phase separation, spherical droplets
G = gel, glassy solid irregular particles
N = no phase separations, clear solution
X = experiment failed, discontinued, dried, microbial contamination etc.

TABLE 25

| well | Reagents | 5 d, +25° C. | 30 d, +4° C. | d, ° C. | d, ° C. |
|---|---|---|---|---|---|
| A1 | 25% PEG 6000 10% 2-propanol pH 4.8 | LL | L, G, A | | |
| A2 | 25% PEG 6000 10% 2-propanol pH 5.3 | LL | L, G, A | | |
| A3 | 25% PEG 6000 10% 2-propanol pH 6.2 | LL | L, G, A | | |
| A4 | 25% PEG 6000 10% 2-propanol pH 7.0 | LL | L, G, A | | |
| A5 | 25% PEG 6000 10% 2-propanol pH 7.4 | LL | L, G, A | | |
| A6 | 25% PEG 6000 10% 2-propanol pH 8.2 | L | L, A | | |
| B1 | 25% PEG 6000 15% 2-propanol pH 4.8 | LL | L, G, A | | |
| B2 | 25% PEG 6000 15% 2-propanol pH 5.3 | LL | L, G, A | | |
| B3 | 25% PEG 6000 15% 2-propanol pH 6.2 | LL | L, G, A | | |
| B4 | 25% PEG 6000 10% 2-propanol pH 7.0 | LL | L, G, A | | |
| B5 | 25% PEG 6000 15% 2-propanol pH 7.4 | L | L, G, A | | |
| B6 | 25% PEG 6000 15% 2-propanol pH 8.2 | L | L, G, A | | |
| C1 | 25% PEG 6000 20% 2-propanol pH 4.8 | LL | L, G, A | | |
| C2 | 25% PEG 6000 20% 2-propanol pH 5.3 | LL | L, G, A | | |
| C3 | 25% PEG 6000 20% 2-propanol pH 6.2 | LL | L, G, A | | |

TABLE 25-continued

| well | Reagents | 5 d, +25° C. | 30 d, +4° C. | d, ° C. | d, ° C. |
|---|---|---|---|---|---|
| C4 | 25% PEG 6000 20% 2-propanol pH 7.0 | LL | L, A | | |
| C5 | 25% PEG 6000 20% 2-propanol pH 7.4 | LL | L, A | | |
| C6 | 25% PEG 6000 20% 2-propanol pH 8.2 | L | L, A | | |
| D1 | 25% PEG 6000 30% 2-propanol pH 4.8 | L,G | X | | |
| D2 | 25% PEG 6000 30% 2-propanol pH 5.3 | L | L, G | | |
| D3 | 25% PEG 6000 30% 2-propanol pH 6.2 | LG | L, G, A | | |
| D4 | 25% PEG 6000 30% 2-propanol pH 7.0 | L | L, A | | |
| D5 | 25% PEG 6000 30% 2-propanol pH 7.4 | LG | A, G | | |
| D6 | 25% PEG 6000 30% 2-propanol pH 8.2 | LG | X | | |

Sample: GTC hSA: labeled 7F-5AC
25% PEG 6000 and 10–30% 2-propanol buffered with 0.1 M K—Na-phosphates pH 4.8–8.2
row A: 25% PEG 6000 and 10% 2-propanol with buffers pH 4.8, 5.3, 6.2, 7.0, 7.4 and 8.2
row B: 25% PEG 6000 and 15% 2-propanol with buffers pH 4.8, 5.3, 6.2, 7.0, 7.4 and 8.2
row C: 25% PEG 6000 and 20% 2-propanol with buffers pH 4.8, 5.3, 6.2, 7.0, 7.4 and 8.2
row D: 25% PEG 6000 and 30% 2-propanol with buffers pH 4.8, 5.3, 6.2, 7.0, 7.4 and 8.2
Results: Strong liquid phase separation in all samples, gel phase in 30% 2-propanol.
Start date (d, m, y): 15.8.2001
Sample: GTC hSA: labeled 7F-5AC
Drop: 5 µl sample + 1 µl reagent
Temperatures +25° C. or +4° C.
Initial protein concentration: 12.2 mg/ml
Final protein concentration: 73 mg/ml
Buffers: 0.1 M K—Na-phosphates pH 4.8–8.2
Microscopy observations
C = crystals
A = amorphous precipitate
L = liquid phase separation, spherical droplets
G = gel, glassy solid irregular particles
N = no phase separations, clear solution
X = experiment failed, discontinued, dried, microbial contamination etc.

Recombinant Production

A growing number of recombinant proteins are being developed for therapeutic and diagnostic applications. However, many of these proteins may be difficult or expensive to produce in a functional form and/or in the required quantities using conventional methods. Conventional methods involve inserting the gene responsible for the production of a particular protein into host cells such as bacteria, yeast, or mammalian cells, e.g., COS or CHO cells, and then growing the cells in culture media. The cultured cells then synthesize the desired protein. Traditional bacteria or yeast systems may be unable to produce many complex proteins in a functional form. While mammalian cells can reproduce complex proteins, they are generally difficult and expensive to grow, and often produce only mg/L quantities of protein. In addition, non-secreted proteins are relatively difficult to purify from procaryotic or mammalian cells as they are not secreted into the culture medium.

In general, the transgenic technology features, a method of making and secreting a protein which is not normally secreted (a non-secreted protein). The method includes expressing the protein from a nucleic acid construct which includes:

(a) a promoter, e.g., a mammary epithelial specific promoter, e.g., a milk protein promoter;

(b) a signal sequence which can direct the secretion of a protein, e.g. a signal sequence from a milk specific protein;

(c) optionally, a sequence which encodes a sufficient portion of the amino terminal coding region of a secreted protein, e.g., a protein secreted into milk, to allow secretion, e.g., in the milk of a transgenic mammal, of the non-secreted protein; and (d) a sequence which encodes a non-secreted protein, wherein elements (a), (b), optionally (c), and (d) are preferably operatively linked in the order recited.

In preferred embodiments: elements a, b, c (if present), and d are from the same gene; the elements a, b, c (if present), and d are from two or more genes.

In preferred embodiments the secretion is into the milk of a transgenic mammal.

In preferred embodiments: the signal sequence is the β-casein signal sequence; the promoter is the β-casein promoter sequence.

In preferred embodiments the non-secreted protein-coding sequence: is of human origin; codes for a truncated, nuclear, or a cytoplasmic polypeptide; codes for human serum albumin or other desired protein of interest.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

Milk Specific Promoters

The transcriptional promoters useful in practicing the present invention are those promoters that are preferentially activated in mammary epithelial cells, including promoters that control the genes encoding milk proteins such as caseins, beta lactoglobulin (Clark et al., (1989) *Bio/Technology* 7: 487–492), whey acid protein (Gorton et al. (1987) *Bio/Technology* 5: 1183–1187), and lactalbumin (Soulier et al., (1992) *FEBS Letts.* 297: 13). Casein promoters may be derived from the alpha, beta, gamma or kappa casein genes of any mammalian species; a preferred promoter is derived from the goat beta casein gene (DiTullio, (1992) *Bio/Technology* 10:74–77). The milk-specific protein promoter or the promoters that are specifically activated in mammary tissue may be derived from either cDNA or genomic sequences. Preferably, they are genomic in origin.

DNA sequence information is available for all of the mammary gland specific genes listed above, in at least one, and often several organisms. See, e.g., Richards et al., *J. Biol. Chem.* 256, 526–532 (1981) (α-lactalbumin rat); Campbell et al., *Nucleic Acids Res.* 12, 8685–8697 (1984) (rat WAP); Jones et al., *J. Biol. Chem.* 260, 7042–7050 (1985) (rat β-casein); Yu-Lee & Rosen, *J. Biol. Chem.* 258, 10794–10804 (1983) (rat γ-casein); Hall, *Biochem. J.* 242, 735–742 (1987) (α-lactalbumin human); Stewart, *Nucleic Acids Res.* 12, 389 (1984) (bovine αs1 and κ casein cDNAs); Gorodetsky et al., *Gene* 66, 87–96 (1988) (bovine β casein); Alexander et al., *Eur. J. Biochem.* 178, 395–401 (1988) (bovine κ casein); Brignon et al., *FEBS Lett.* 188, 48–55 (1977) (bovine αS2 casein); Jamieson et al., *Gene* 61, 85–90 (1987), Ivanov et al., *Biol. Chem.* Hoppe-Seyler 369, 425–429 (1988), Alexander et al., *Nucleic Acids Res.* 17, 6739 (1989) (bovine β lactoglobulin); Vilotte et al., *Biochimie* 69, 609–620 (1987) (bovine α-lactalbumin). The structure and function of the various milk protein genes are reviewed by Mercier & Vilotte, *J. Dairy Sci.* 76, 3079–3098 (1993) (incorporated by reference in its entirety for all purposes). To the extent that additional sequence data might be required, sequences flanking the regions already obtained could be readily cloned using the existing sequences as probes. Mammary-gland specific regulatory sequences from different organisms are likewise obtained by screening libraries from such organisms using known cognate nucleotide sequences, or antibodies to cognate proteins as probes.

Signal Sequences

Among the signal sequences that are useful in accordance with this invention are milk-specific signal sequences or other signal sequences which result in the secretion of eukaryotic or prokaryotic proteins. Preferably, the signal sequence is selected from milk-specific signal sequences, i.e., it is from a gene which encodes a product secreted into milk. Most preferably, the milk-specific signal sequence is related to the milk-specific promoter used in the expression system of this invention. The size of the signal sequence is not critical for this invention. All that is required is that the sequence be of a sufficient size to effect secretion of the desired recombinant protein, e.g., in the mammary tissue. For example, signal sequences from genes coding for caseins, e.g., alpha, beta, gamma or kappa caseins, beta lactoglobulin, whey acid protein, and lactalbumin are useful in the present invention. The preferred signal sequence is the goat β-casein signal sequence.

Signal sequences from other secreted proteins, e.g., proteins secreted by liver cells, kidney cell, or pancreatic cells can also be used.

Transgenic Mammals

The DNA constructs of the protein of interest, in this case human serum albumin, are introduced into the germ line of a mammal. For example, one or several copies of the construct may be incorporated into the genome of a mammalian embryo by standard transgenic techniques.

Any non-human mammal can be usefully employed in this invention. Mammals are defined herein as all animals, excluding humans, that have mammary glands and produce milk. Preferably, mammals that produce large volumes of milk and have long lactating periods are preferred. Preferred mammals are cows, sheep, goats, mice, oxen, camels and pigs. Of course, each of these mammals may not be as effective as the others with respect to any given expression sequence of this invention. For example, a particular milk-specific promoter or signal sequence may be more effective in one mammal than in others. However, one of skill in the art may easily make such choices by following the teachings of this invention.

Although the foregoing invention has been described in some detail by way of illustration and example for purposes of understanding, it will be apparent to those skilled in the art that certain changes and modifications may be practiced. Therefore, the description and examples should not be construed as limiting the scope of the invention, which is delineated by the appended claims.

It should also be noted that while albumin is crystallized with various compounds, ethanol and mineral salts including phosphates industrial methods for crystallization with phosphates are not found in the literature. Through the preferred embodiments of the current invention it has now been found that human albumin can be crystallized advantageously with phosphate salts by utilizing in full extent the invented key process parameters and/or conditions of the current invention. The invented parameters and some variations thereof are listed and described above.

Accordingly, it is to be understood that the embodiments of the invention herein providing for crystallized and purified human albumin are merely illustrative of the application of the principles of the invention. It will be evident from the foregoing description that changes in the form, methods of use, and applications of the elements of the disclosed may be resorted to without departing from the spirit of the invention, or the scope of the appended claims.

PRIOR ART CITATIONS INCORPORATED BY REFERENCE

1. Andersson, 1966, *"The Heterogeneity Of Bovine Serum Albumin,"* BIOCHIM. BIOPHYS. ACTA. 117:115–133.
2. Carter D C, et al., *Crystals Of Serum Albumin For Use In Genetic Engineering And Rational Drug Design*, U.S. Pat. No. 5,585,466.
3. Carter D C, et al., *Human Serum Albumin Crystals and Method of Preparation*, European Patent Application # 0 357 857 A1.
4. Carter D C, et al., *Preliminary Crystallographic Studies of Four Crystals Forms of Serum Albumin*, EUR J BIOCHEM (1994); 226: 1049–1052.
5. Carter D C, et al., *Three-Dimensional Structure of Human Serum Albumin*, SCIENCE (1989) 244:1195–1198.
6. Cochrane et al., *Human Albumin Administration In Critically Ill Patients: Systematic Review Of Randomized Controlled Trials.* BR MED J. (1998);317:235–240.
7. Cohn E J, et al., *Preparation and Properties of Serum and Plasma Proteins. XIII. Crystallization of Serum Albumins from Ethanol-Water Mixtures*, J. AM. CHEM. SOC. (1947) 69: 1753–1761.
8. Cohn E J, et al., 1946, *"Preparation And Properties Of Serum And Plasma Proteins. IV. A System For The Separation Into Fractions Of The Protein And Lipoprotein Components Of Biological Tissues And Fluids,"* J. AM. CHEM. SOC. 68:459–475.

9. Copelin C. et al., *Practical Points In The Use Of Albumin For Hypovolemia*. J Peranesth Nurs. (1998)13:118–120.
10. Dale L B, et al., *G Protein-Coupled Receptor Kinase-Mediated Desensitization of Metabotropic Glutamate Receptor 1A Protects Against Cell Death*, J Biol Chem (2000); 275: 38213–38220.
11. Emerson T E, *Unique Features of Albumin: A Brief Review*, Crit Care Med. (1989) 17:690–693.
12. Goldwaser P, et al., *Association of Serum Albumin And Mortality Risk*, J. Clin Epidemiol. (1997) 50:693–703.
13. Gore D C, et al., *Colloid Infusions Reduce Glomerular Being filtered In Resuscitated Burn Patients*. J. Trauma. (1996) 3:356–360.
14. Haupt H and K Heide, *Crystallization of Human Albumin Using Mineral Salts*, Klin Wochenschr (1967); 45: 726–729.
15. Hughes and Dintzis, 1964, "*Crystallization of the mercury dimers of human and bovine mercaptalbumin,*" J. Biol. Chem. 239:845–849.
16. Hughes W L, *An Albumin Fraction Isolated From Human Plasma as a Crystalline Mercuric Salt*, J. Am. Chem. Soc. (1947); 69: 1836–1837.
17. Klein G L, et al., *The Aluminum Content of Parenteral Solutions: Current Status*. Nutr. Rev. (1991) 49:74–79.
18. Kovalik S G, et al., *The Cardiac Effect of Altered Calcium Hemostasis After Albumin Resuscitation*, J. Trauma. (1981) 21:275–279.
19. Ledgerwood A M, et al., *Post-Resuscitation Hypertension, Etiology, Morbidity, And Treatment*. Arch. Surg. (1974);108:531–538.
20. Lewin J, *Preparation and Properties of Serum and Plasma Proteins. XXX. Crystalline Derivatives of Human Serum Albumin and of Certain Other Proteins*, J. Am. Chem. Soc. (1951); 73: 3906–3911.
21. Low B W, *Preparation and Properties of Serum and Plasma Proteins. XXXIV. An X-Ray Study of Crystalline Human Serum Albumin Preparations*, J. Am. Chem. Soc. (1952); 74: 4830–4834.
22. Low B W and E J Weichel, *Preparation and Properties of Serum and Plasma Proteins. XXXI. An Optical and Morphological Study of Some Crystalline Human Serum Albumin Preparations and of Their Derivatives*, J. Am. Chem. Soc. (1951); 73: 3911–3916.
23. Peters T. *Serum Albumin*, Adv. Protein Chem 37:161–245. (1985).
24. Rainey T G, et al., Pharmacology Of Colloids And Crystalloids. In: *The Pharmacologic Approach to the Critically Ill Patient*, (Chemow B. ed); (Williams and Wilkins, Baltimore Md. Publ.) (1994) pages 272–290.
25. Rao S N, et al., *Preliminary X-Ray Investigation of an Orthorhombic Crystal Form of Human Plasma Albumin*, J Biol Chem (1976) 251: 3191–3193.
26. Roberts J S, et al., *Colloid Volume Expanders: Problems, Pitfalls, and Possibilities*. Drugs. 1998;55:621–630.
27. Sollenne et al., "*Disruption Of The Tryptophan Binding Site In The Human Serum Albumin Dimer,*" Arch. Biochem. Biophys. 207:264–269 (1981).
28. Sugio S, et al., *Crystal Structure of Human Serum Albumin At 2.5 A Resolution*, Protein Eng (1999) 12: 439–446.
29. Tullis J L, et al., *Albumin: Background and Use*. JAMA. (1977) 237:355–360.
30. Vermeulen L C et al., *Guidelines for the Use of Albumin, Nonprotein Colloids, and Crystalloid Solutions*, Arch Intern Med. (1995) 155:373–379.

What claimed is:

1. A method of producing crystalline human albumin comprising:
    a) concentrating an albumin containing fluid until said fluid has at least 15 grams of albumin per liter of solution;
    b) adding a first phosphate mixture to said albumin containing fluid until the concentration of said phosphate mixture is in the range of 2.4–2.6 molar;
    c) providing a first filtering of said albumin containing solution so as to form a resultant crystallizing batch solution to remove impurities;
    d) cooling the resultant filtrate of said crystallizing batch solution to a temperature of at most 15° C.;
    e) allowing the human albumin in said crystallizing batch solution to crystallize;
    f) adding more of said first phosphate mixture to said crystallizing batch solution sufficient to achieve a concentration of at most 3.0 molar;
    g) making a first separation of albumin crystals from any remaining fluid;
    h) suspending the albumin crystals from said first separation of albumin crystals in a second phosphate mixture wherein said second phosphate mixture has a concentration of 2.7–3.0 M;
    i) heating the crystal suspension from said first separation of albumin crystals up to temperature in the range of 40–50° C. in order to dissolve the crystals,
    j) providing a second filtering to the dissolved crystal suspension from said first separation of albumin crystals;
    k) cooling the resultant dissolved crystal suspension from said first separation of albumin crystals to a temperature of at most 15° C.; and
    l) allowing albumin crystals to form the resultant cooled crystal suspension;
    wherein the application of these specific steps allows the purification and crystallization of human albumin from a given human albumin containing feedstream.

2. The method of claim 1 wherein said first phosphate mixture is comprised of a sodium phosphate salt.

3. The method of claim 1 wherein said first phosphate mixture is a potassium phosphate salt.

4. The method of claim 1 wherein said first phosphate mixture is comprised of both a sodium and a potassium salt.

5. The method of claim 1 wherein said albumin containing fluid has a concentration of albumin in one liter of solution in a range of 15–50 grams.

6. The method of claim 1 wherein the temperature of said first phosphate mixture at the time of addition is in the range of 20–30° C.

7. The method of claim 1 wherein said first phosphate mixture at the time of addition has a pH in the range of pH 6.0–6.7.

8. The method of claim 1 wherein said filtrate collected after filtering said crystallizing batch is cooled to a temperature of at most 10° C.

9. The method of claim 1 wherein said crystallizing batch solution is allowed to crystallize for at most 12 hours.

10. The method of claim 1 wherein said crystallizing batch solution is allowed to crystallize for at most 24 hours.

11. The method of claim 1 wherein said crystallizing batch solution is allowed to crystallize for at least 24 hours.

12. The method of claim 1 wherein said first separation of albumin crystals is accomplished by filtration.

13. The method of claim 1 wherein said first separation of albumin crystals is accomplished by centrifugation.

14. The method of claim 1 wherein said first separation of albumin crystals is accomplished by gravity.

15. The method of claim 1 wherein after said first separation of albumin crystals, the crystals are dried.

16. The method of claim 1 wherein said second phosphate mixture is comprised of a sodium phosphate salt.

17. The method of claim 1 wherein said second phosphate mixture is a potassium phosphate salt.

18. The method of claim 1 wherein said second phosphate mixture is comprised of both a sodium and a potassium salt.

19. The method of claim 1 wherein said albumin containing fluid is previously clarified to remove impurities not in solution.

20. The method according to claim 1 wherein the pH of said resultant crystallizing batch solution is 5.6–7.8.

21. The method according to claim 1 wherein the pH of said resultant crystallizing batch solution is 6.0–6.5.

22. The method according to claim 1 wherein the pH of said resultant crystallizing batch solution is 7.0–7.8.

23. The method according to claim 1 wherein said the concentration of said first phosphate mixture has a concentration in the range of 2.2–3.0 M.

24. The method of claim 1 wherein said albumin containing fluid has an albumin concentration in a range of 2–400 grams per liter of solution.

25. The method of claim 1 wherein said albumin containing fluid has an albumin concentration in a range of 3–300 grams per liter of solution.

26. The method of claim 1 wherein said albumin containing fluid has an albumin concentration in a range of 3–100 grams per liter of solution.

27. The method of claim 1 wherein said albumin containing fluid has an albumin concentration in a range of 3–40 grams per liter of solution.

28. The method of claim 1 wherein said albumin containing fluid has an albumin concentration in a range of 2–10 grams per liter of solution.

29. The method of claim 1 wherein said crystalline human albumin product is utilized as an excipient in pharmaceutical preparations.

30. The method of claim 1 wherein said crystalline human albumin product is utilized as a therapeutic agent in a pharmaceutical composition.

31. The method of claim 1 wherein said crystalline human albumin product is utilized to treat a medical condition selected from the group consisting of edema, hypovolemia, hypoalbuminemia, Adult Respiratory Disease Syndrome (ARDS), nephrosis, severe burn, and hypoproteinemia.

32. The method of claim 1 wherein said crystalline human albumin product is utilized during cardiopulmonary bypass surgery.

33. The method of claim 1 wherein said dissolved crystal suspension from said first separation of albumin crystals is cooled to a temperature of at most 10° C.

34. The method of claim 33 wherein the albumin crystals precipitating out of the dissolved crystal suspension are dissolved back into solution again and re-crystallized at least once.

35. The method of claim 1 wherein said feedstream is milk or other bodily fluid from a transgenic mammal.

36. The method of claim 35 wherein milk from a transgenic mammal is clarified to remove impurities and some milk proteins.

37. The method of claim 35 wherein the level of purity in a given feedstream is at least 10%, that is, wherein human albumin constitutes at least 10% of the total protein of a given solution.

38. The method of claim 1 wherein said feedstream is a culture supernatant or bodily fluid from a host which expresses recombinant human albumin.

39. The method of claim 38 wherein said host is a mammalian cell.

40. The method of claim 38 wherein said host is a yeast cell.

41. The method of claim 38 wherein said host is an insect cell.

42. The method of claim 38 wherein said host is a prokaryotic cell.

43. A method of producing crystalline human albumin comprising:
   a) concentrating an albumin containing fluid until said fluid has at least 15 grams of albumin per liter of solution;
   b) adding a sufficient amount of a first chemical modifying agent selected from the group consisting of polyethylene glycol. $(NH_4)SO_4$, Propanol, Benzyl Alcohol, and Potassium Chloride to said albumin containing fluid;
   c) providing a first filtering of said albumin containing solution so as to form a resultant crystallizing batch solution to remove impurities;
   d) cooling the resultant filtrate of said crystallizing batch solution to a temperature of at most 20° C.;
   e) allowing the human albumin in said crystallizing batch solution to crystallize;
   f) adding more of said first chemical modifying agent to said crystallizing batch solution sufficient to achieve a concentration of at most 3.0 molar;
   g) making a first separation of albumin crystals from any remaining fluid;
   h) suspending the albumin crystals from said first separation of albumin crystals in a second chemical modifying agent selected from the group consisting of decanol, caprylic acid, $MgCl_2$, Ammonium Acetate, and 2-Propanol;
   i) heating the crystal suspension from said first separation of albumin crystals up to temperature in the range of 40–50° C. in order to dissolve the crystals,
   j) providing a second filtering to the dissolved crystal suspension from said first separation of albumin crystals;
   k) cooling the resultant dissolved crystal suspension from said first separation of albumin crystals to a temperature of at most 15° C.; and
   l) allowing albumin crystals to form the resultant cooled crystal suspension;
wherein the application of these specific steps allows the purification and crystallization of human albumin from a given human albumin containing feedstream.

44. The method of claim 43 wherein said first chemical modifying agent is Polyethylene Glycol and said second chemical modifying agent is decanol.

45. The method of claim 43 wherein said first chemical modifying agent is $(NH_4)_2SO_4$ and said second chemical modifying agent is decanol.

46. The method of claim 43 wherein said first chemical modifying agent is Polyethylene Glycol and said second chemical modifying agent is caprylic acid.

47. The method of claim 43 wherein said first chemical modifying agent is $(NH_4)_2SO_4$ and said second chemical modifying agent is caprylic acid.

48. The method of claim 43 wherein said first chemical modifying agent is 2-Propanol and said second chemical modifying agent is $MgCl_2$.

49. The method of claim 43 wherein said first chemical modifying agent is Benzyl Alcohol and said second chemical modifying agent is $MgCl_2$.

50. The method of claim 43 wherein said first chemical modifying agent is Polyethylene Glycol and said second chemical modifying agent is Ammonium Acetate.

51. The method of claim 43 wherein said first chemical modifying agent is Polyethylene Glycol and said second chemical modifying agent is 2-Propanol.

* * * * *

UNITED STATES PATENT AND TRADEMARK OFFICE
CERTIFICATE OF CORRECTION

PATENT NO. : 7,087,719 B2
APPLICATION NO. : 10/300233
DATED : August 8, 2006
INVENTOR(S) : Visuri et al.

It is certified that error appears in the above-identified patent and that said Letters Patent is hereby corrected as shown below:

On the Title page (73) insert the correct Assignee as follows:

Assignee: Taurus hSA, LLC

Framingham, MA (US)

Signed and Sealed this

Sixth Day of January, 2009

JON W. DUDAS
*Director of the United States Patent and Trademark Office*